(12) United States Patent
Johal et al.

(10) Patent No.: US 8,409,875 B2
(45) Date of Patent: Apr. 2, 2013

(54) MEASUREMENT OF BINDING KINETICS WITH A RESONATING SENSOR

(75) Inventors: Gaganbir Singh Johal, Hudson, WI (US); Ian Robert Harmon, Hudson, WI (US); Richard Allen Van Deusen, Hudson, WI (US)

(73) Assignee: Rapid Diagnostek, Inc., Hudson, WI (US)

( * ) Notice: Subject to any disclaimer, the term of this patent is extended or adjusted under 35 U.S.C. 154(b) by 0 days.

(21) Appl. No.: 13/278,032

(22) Filed: Oct. 20, 2011

(65) Prior Publication Data

US 2012/0100636 A1    Apr. 26, 2012

Related U.S. Application Data

(60) Provisional application No. 61/405,048, filed on Oct. 20, 2010.

(51) Int. Cl.
*G01N 33/566* (2006.01)
(52) U.S. Cl. ..................................... 436/501; 435/283.1
(58) Field of Classification Search .................. None
See application file for complete search history.

(56) References Cited

U.S. PATENT DOCUMENTS

| | | | |
|---|---|---|---|
| 4,155,257 A | 5/1979 | Wittke | |
| 4,177,669 A | 12/1979 | Wenger | |
| 5,135,852 A | 8/1992 | Ebersole et al. | |
| 5,367,308 A | 11/1994 | Weber | |
| 5,404,628 A | 4/1995 | Ketcham | |
| 5,595,908 A | 1/1997 | Fawcett et al. | |
| 5,807,758 A | 9/1998 | Lee et al. | |
| 5,837,885 A | 11/1998 | Goodbread et al. | |
| 5,922,594 A | 7/1999 | Löfås | |
| 5,932,953 A | 8/1999 | Drees et al. | |
| 5,936,150 A | 8/1999 | Kobrin et al. | |
| 6,033,852 A | 3/2000 | Andle et al. | |
| 6,087,187 A | 7/2000 | Wiegand et al. | |
| 6,156,578 A | 12/2000 | Tom | |
| 6,165,335 A | 12/2000 | Lennox et al. | |
| 6,205,315 B1 | 3/2001 | Montfort et al. | |
| 6,237,417 B1 | 5/2001 | Lonsdale et al. | |
| 6,247,354 B1 | 6/2001 | Vig et al. | |
| 6,321,444 B1 | 11/2001 | Yatsuda et al. | |

(Continued)

FOREIGN PATENT DOCUMENTS

WO   WO2004057319   7/2004
WO   WO2010106331   9/2010

OTHER PUBLICATIONS

Lakovkin et al., Highly Sensitive Saw Sensors 1994 IEEE International Frequency Control Symposium. pp. 395-400.

(Continued)

*Primary Examiner* — N. C. Yang
(74) *Attorney, Agent, or Firm* — Patterson Thuente Pedersen, PA

(57) ABSTRACT

A subject material in a fluid sample is detected using a resonating sensor immersible in the fluid sample. Binding kinetics of an interaction of an analyte material present in the fluid sample are measured with the resonating sensor, which has binding sites for the analyte material. Prior to exposing the resonating sensor to the fluid sample, operation of the resonating sensor is initiated, producing a sensor output signal representing a resonance characteristic of the resonating sensor. Optionally, a reference resonator that lacks binding sites for the analyte is used to produce a reference output signal. Introduction of a fluid sample to the resonating sensor is automatically detected based on a characteristic change in the sensor output signal or a reference output signal. In response to the detecting of the introduction of the fluid sample, automated measurement of the binding kinetics are measured.

14 Claims, 12 Drawing Sheets

U.S. PATENT DOCUMENTS

| | | |
|---|---|---|
| 6,336,353 B2 | 1/2002 | Matsiev et al. |
| 6,441,703 B1 | 8/2002 | Panasik |
| 6,452,310 B1 | 9/2002 | Panasik |
| 6,461,490 B1 | 10/2002 | Lennox et al. |
| 6,467,351 B2 | 10/2002 | Lonsdale et al. |
| 6,494,079 B1 | 12/2002 | Matsiev et al. |
| 6,557,416 B2 | 5/2003 | Chang et al. |
| 6,589,798 B1 | 7/2003 | Löfås et al. |
| 6,630,309 B2 | 10/2003 | Willner et al. |
| 6,647,764 B1 | 11/2003 | Paul et al. |
| 6,651,488 B2 | 11/2003 | Larson et al. |
| 6,668,618 B2 | 12/2003 | Larson et al. |
| 6,673,533 B1 | 1/2004 | Wohlstadter et al. |
| 6,787,368 B1 | 9/2004 | Wong et al. |
| 6,848,299 B2 | 2/2005 | Paul et al. |
| 6,851,313 B2 | 2/2005 | Fehrenbach |
| 7,036,375 B2 | 5/2006 | Nozaki |
| 7,053,533 B2 | 5/2006 | Thanner et al. |
| 7,093,482 B2 | 8/2006 | Berndt |
| 7,135,295 B1 | 11/2006 | Willner et al. |
| 7,138,238 B2 | 11/2006 | Vodyanoy et al. |
| 7,168,298 B1 | 1/2007 | Manginell et al. |
| 7,171,844 B2 | 2/2007 | Cunningham et al. |
| 7,178,378 B2 | 2/2007 | Crawley et al. |
| 7,201,041 B2 | 4/2007 | Itoh et al. |
| 7,210,332 B2 | 5/2007 | Kolosov et |
| 7,282,834 B2 | 10/2007 | Kubena et al. |
| 7,285,736 B2 | 10/2007 | Korpi |
| 7,305,883 B2 | 12/2007 | Khuri-Yakub et al. |
| 7,320,879 B2 | 1/2008 | Karlsson et al. |
| 7,331,232 B2 | 2/2008 | Itoh et al. |
| 7,334,452 B2 | 2/2008 | Matsiev et al. |
| 7,353,695 B2 | 4/2008 | Fitch et al. |
| 7,389,673 B2 | 6/2008 | Kimura et al. |
| 7,398,671 B2 | 7/2008 | Brederlow et al. |
| 7,427,819 B2 | 9/2008 | Hoen et al. |
| 7,437,907 B2 | 10/2008 | Kimura et al. |
| 7,458,265 B2 | 12/2008 | Shih et al. |
| 7,464,580 B2 | 12/2008 | Zeng et al. |
| 7,468,608 B2 | 12/2008 | Feucht et al. |
| 7,473,551 B2 | 1/2009 | Warthoe et al. |
| 7,479,685 B2 | 1/2009 | Fazzio et al. |
| 7,509,860 B2 | 3/2009 | Lee et al. |
| 7,525,398 B2 | 4/2009 | Nishimura et al. |
| 7,552,619 B2 | 6/2009 | Andle |
| 7,555,952 B2 | 7/2009 | Onishi et al. |
| 7,570,125 B2 | 8/2009 | Ostanin et al. |
| 7,616,073 B1 | 11/2009 | Taheri et al. |
| 7,650,788 B2 | 1/2010 | Edmonson et al. |
| 7,659,654 B2 | 2/2010 | Kondo |
| 7,681,433 B2 | 3/2010 | Konno et al. |
| 7,690,256 B2 | 4/2010 | Ishii et al. |
| 7,694,552 B2 | 4/2010 | Khuri-Yakub et al. |
| 7,721,590 B2 | 5/2010 | Kolosov et al. |
| 7,724,103 B2 | 5/2010 | Feng et al. |
| 7,763,475 B2 | 7/2010 | Klenerman et al. |
| 7,795,008 B2 | 9/2010 | Dayagi et al. |
| 7,795,997 B2 | 9/2010 | Larson et al. |
| 7,845,230 B2 | 12/2010 | Oita et al. |
| 7,888,134 B2 | 2/2011 | Zeng et al. |
| 7,925,448 B2 | 4/2011 | Karlsson et al. |
| 7,939,343 B2 | 5/2011 | Li et al. |
| 7,942,056 B2 | 5/2011 | Mutharasan et al. |
| 7,963,151 B2 | 6/2011 | Godfrey et al. |
| 7,969,068 B2 | 6/2011 | Yokobori et al. |
| 7,975,530 B2 | 7/2011 | Whalen et al. |
| 7,993,854 B2 | 8/2011 | Mutharasan et al. |
| 2001/0008081 A1 | 7/2001 | Smith et al. |
| 2004/0187580 A1* | 9/2004 | Nozaki .......................... 73/580 |
| 2005/0148065 A1 | 7/2005 | Zhang et al. |
| 2006/0107733 A1 | 5/2006 | Aastrup et al. |
| 2006/0133952 A1* | 6/2006 | Zhang et al. ............... 435/287.2 |
| 2006/0133953 A1 | 6/2006 | Zhang et al. |
| 2007/0023621 A1 | 2/2007 | Blick et al. |
| 2009/0084678 A1 | 4/2009 | Joshi et al. |
| 2009/0199639 A1 | 8/2009 | Konno et al. |
| 2009/0282902 A1 | 11/2009 | Warthoe |
| 2009/0288488 A1 | 11/2009 | Yamakawa et al. |
| 2010/0021346 A1 | 1/2010 | Wakamatsu et al. |
| 2010/0107285 A1 | 4/2010 | Ekinci et al. |
| 2010/0154544 A1 | 6/2010 | Paci et al. |
| 2010/0180673 A1 | 7/2010 | Cable et al. |
| 2010/0207602 A1 | 8/2010 | Loverich et al. |
| 2010/0233032 A1 | 9/2010 | Frogley et al. |
| 2010/0236322 A1 | 9/2010 | Kogai et al. |
| 2010/0313636 A1 | 12/2010 | Wakamatsu et al. |
| 2011/0101996 A1 | 5/2011 | Potyrailo et al. |

OTHER PUBLICATIONS

Apapov et al., "Leaky Waves in Solid-Liquid-Solid Systems. Acoustoelectronic Microanalysis of Viscous-Elastic Properties for Liquids for Biological Nature". Physical Acoustics Fundamentals and Applications. Edited by Leroy et al., Plenum Press. New York 1991. pp. 213-217.

International Search Report and Written Opinion from International Application No. PCT/US2011/057147 dated May 2, 2012.

* cited by examiner

MEASUREMENT OF BINDING KINETICS WITH A RESONATING SENSOR

PRIOR APPLICATION

This application claims the benefit of U.S. Provisional Application No. 61/405,048 filed Oct. 20, 2010, entitled "RESONATOR OPERATING FREQUENCY OPTIMIZATION FOR PHASE-SHIFT DETECTION SENSORS," the disclosure of which is incorporated by reference herein in its entirety.

FIELD OF THE INVENTION

The present invention relates to measurement and testing, and more specifically to piezoelectric resonator sensors and associated methods for diagnostic measuring or testing using the principle of a phase or frequency shift from an initial resonance point in response to exposure of the sensors to certain materials.

BACKGROUND OF THE INVENTION

There are a variety of instruments and measurement techniques for diagnostic testing of materials related to human health, veterinary medical, environmental, biohazard, bioterrorism, agricultural commodity and food safety. Still, a solution for diagnostic testing and analysis of chemical or biological materials at the point of need remains limited. Diagnostic testing traditionally requires long response times to obtain meaningful data, involves expensive remote or cumbersome laboratory equipment that costs thousands of dollars located in a centralized laboratory, requires large sample sizes, utilizes multiple reagents, demands highly trained users, may require numerous steps, and/or involves significant direct and indirect costs. For instance, in both the veterinary and human diagnostic markets, most tests require that a specimen be collected from the patient and sent to the laboratory, but the results are not available for several hours or days later. As a result, the patient may leave the caregiver's office without confirmation of the diagnosis and the opportunity to begin immediate treatment.

Other problems related to portable devices include diagnostic results that are limited in sensitivity and reproducibility compared to in-laboratory testing. Fast response times are desirable and often critical to the identification of chemical and/or biological materials, such as in providing timely medical attention or in averting the spread or exposure of public health threats. Direct costs relate to the labor, procedures, and equipment required for each type of analysis. Indirect costs partially accrue from the delay time before actionable information can be obtained, e.g., in medical analyses or in the monitoring of chemical processes. Many experts believe that the simultaneous diagnosis and treatment enabled by an effective point of need diagnostic testing system would yield clinical, economic and social benefits.

Biosensors based on piezoelectric properties of materials have been used in detecting very small quantities of materials. Piezoelectric resonators used as sensors in such applications are sometimes called "micro-balances." A piezoelectric resonator is typically constructed as a thin planar layer of crystalline piezoelectric material sandwiched between two electrode layers. When used as a sensor, the resonator is coated with a binding layer which, when exposed to the material being detected, allows the material to bind to the surface of the resonator. Modern resonators are fabricated using MEMS techniques and can be constructed to be so small that their resonant frequency is on the gigahertz scale. In general, resonators having higher resonant frequencies are more sensitive.

The conventional way of detecting the amount of the material bound on the surface of a sensing resonator is to operate the resonator as an oscillator at its resonant frequency. As the material being detected binds on the resonator surface, the mass of the resonator increases and the resonant frequency of oscillation is consequently reduced. The change in the resonant frequency of the resonator over time, presumably caused by the binding of the material on the resonator surface, is indicative of the amount of the material that is bound on the resonator or the rate at which the material accumulates on the resonator surface. From this data, a concentration of the material of interest, or analyte, present in the sample can be computed.

Conventionally, biosensors of this type generally include an assembly in which an intrinsic biosensor is surrounded by at least one fluidic channel, which is coupled to a sample reservoir for presenting a sample to the biosensor in a controlled manner. Most conventional biosensor configurations also include a mechanism for controlling and maintaining a desired temperature of the sample as it is presented to the intrinsic biosensor. In operation, the sample is drawn through the fluidic channel and across the intrinsic biosensor by application of vacuum or similar actuation pressure at a vacuum port. Oftentimes, the sample must be refined prior to introduction into the assembly by the addition of buffer or removal of certain elements such as whole cells or other particulates, which can interfere with the accuracy of the measurements. This refining step can be cumbersome and costly, making such measurements impractical for field applications. In addition, the introduction of the sample changes the physical environment in which the measurement is made. For example, the resonator oscillates at different resonant frequencies when exposed to a liquid sample versus prior to exposure when the resonator is in free air oscillation due to differences in viscosity between the two fluids.

Another approach involves stabilizing the measurement environment prior to introduction of the sample reagent. For instance, one type of instrument has two separate fluid reservoirs in which the first reservoir contains a buffer solution and the second reservoir contains the sample reagent. In operation, the buffer solution is introduced to the biosensor first, and the system is allowed to stabilize. Next, a valve switches to the sample reagent and measurements are made. The introduction of the buffer solution permits the sensor's oscillation to be tuned, or adjusted in accordance with the viscosity and temperature conditions of the buffer, which closely approximates the viscosity and temperature of the sample. The objective of this tuning is to operate the resonator as close as possible to its ideal resonant frequency for maximum sensitivity. One drawback of this approach is the introduced complexities and processing time requirements, which can result in expensive, error-prone, and time-consuming test results.

Another challenge faced by designers of resonant biosensors is in making quantifiable concentration measurements on highly concentrated samples. One trade-off of having the increased sensitivity of micro-scale (or smaller) resonators is their susceptibility to becoming rapidly saturated with analyte. In certain tests, a sensor can become saturated in a matter of seconds or even in a fraction of a second. In this case, although the sensor can operate as a simple detector of the presence of analyte, it cannot accurately measure the rate at which the analyte binds to the sensor, commonly referred to as binding kinetics. Measurement of binding kinetics is needed for quantification of the concentration of the analyte, can be impossible to obtain with any suitable accuracy or repeatability in highly concentrated samples using conventional techniques. Moreover, when analyte begins to bind to the resonator in significant quantity immediately from the moment that the resonant sensor is introduced to the sample, the instrument may not have the time to achieve its required stabilization prior to the taking of measurements, or to perform tuning of the resonator either before or after the taking of measurements, thereby further exacerbating the problem.

In view of the above, a practical solution is needed to enable the measurement of binding kinetics in sensitive instruments, particularly early binding kinetics from the time the sample is introduced to the sensor. Additionally, it would be desirable to perform such measurements without having to undertake the complexity of stabilizing the resonating sensor using a buffer solution or specially-refined sample.

SUMMARY OF THE INVENTION

One aspect of the invention is directed to detecting a presence of a subject material in a fluid sample using at least one resonating sensor immersible in the fluid sample. Binding kinetics of an interaction of an analyte material present in the fluid sample are measured with the resonating sensor, which has binding sites for the analyte material. Prior to exposing the resonating sensor to the fluid sample, operation of the resonating sensor is initiated, which produces a sensor output signal representing a resonance characteristic of the resonating sensor. Optionally, a reference resonator is used that produces a reference output signal. The reference resonator lacks binding sites for the analyte. Introduction of a fluid sample to the resonating sensor is automatically detected based on detection of a characteristic change in the sensor output signal or a reference output signal, or both. In response to the detecting of the introduction of the fluid sample, automated measurement of the binding kinetics of the analyte material to the resonating sensor are measured.

According to another aspect of the invention, an apparatus for measuring binding kinetics of an interaction of an analyte material present in a fluid sample is provided. The apparatus includes a resonator interface adapted be operatively coupled with one or more resonating devices, at least one of which is a sensing resonator having binding sites for the analyte material. The one or more resonating devices are adapted to be driven into an oscillating motion by actuation circuitry. Measurement circuitry is arranged to be coupled to the one or more resonating devices via the resonator interface. The measurement circuitry is configured to measure one or more resonator output signals representing a resonance characteristic of the oscillating motion of the one or more resonating devices. A controller is operatively coupled with the actuation and measurement circuitry, and configured to detect introduction of the fluid sample into contact with the one or more resonating devices based on detection of a characteristic change in the one or more resonator output signals; and in response to the detection of the introduction of the fluid sample, initiate measurement of the binding kinetics of the analyte material to the at least one sensing resonator.

A method for measuring binding kinetics of an interaction of an analyte material present in a fluid sample with one or more resonating devices, at least one of which is a sensing resonator having binding sites for the analyte material, is provided in another aspect of the invention. According to this method, prior to exposing the one or more resonating devices to the fluid sample, operation of the one or more resonating devices is initiated that produces one or more resonator output signals representing a resonance characteristic of each of the one or more of the resonating sensors. Introduction of a fluid sample to the one or more resonating devices is automatically detected based on detection of a characteristic change in the one or more resonator output signals, such as resonance frequency or phase angle, for example. In response to the detecting of the introduction of the fluid sample, automated measurement of the binding kinetics of the analyte material to the at least one resonating sensor having the binding sites is initiated.

The measurement of the binding kinetics can be based on change of a resonance frequency of the one or more resonating devices, which can be a differential mode measurement in some embodiments. The binding kinetics can be based on a total change over time, or on a rate of change measurement.

A number of advantages of the invention will become apparent to persons of skill in the relevant art based on the following description of the preferred embodiments.

BRIEF DESCRIPTION OF THE DRAWINGS

The invention may be more completely understood in consideration of the following detailed description of various embodiments of the invention in connection with the accompanying drawings, in which.

Figure 1A:
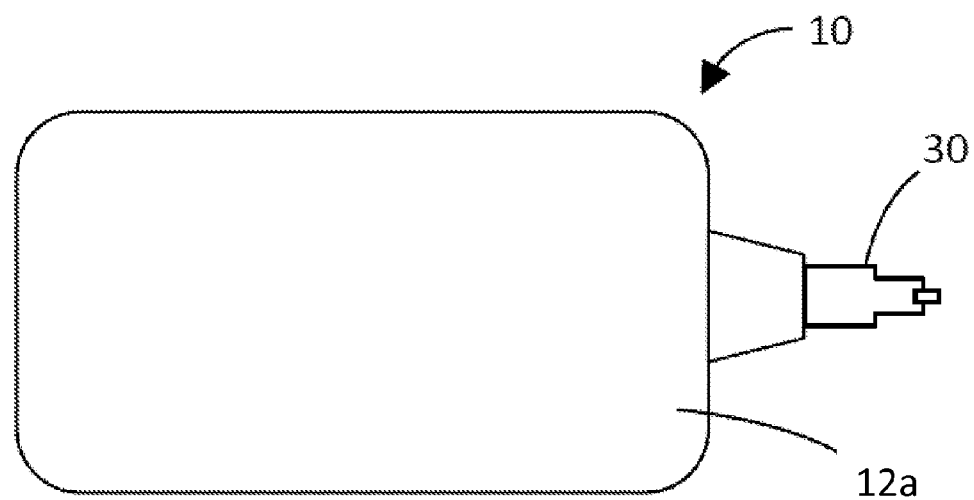
FIG. 1A is a diagram illustrating a hand-held resonance shift detector system according to one embodiment.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

While this invention may be embodied in many different forms, there are described in detail herein specific preferred embodiments of the invention. This description is an exemplification of the principles of the invention and is not intended to limit the invention to the particular embodiments illustrated.

One aspect of the present invention is directed toward a simple, effective, cost-efficient, reliable, repeatable, sensor for resonance shift detection of chemical and/or biological materials that compensates for the variation of the unique resonant frequency in individual resonators. For the sake of brevity, these devices are referred to herein as biosensors, though it should be understood that they can be used to detect materials in samples other than biological samples. Resonance shift detection, in various embodiments, can be based on phase shift or frequency shift. One type of embodiment includes a sensor and resonance shift detection system that can compensate or adjust for the variation in individual resonator frequency and environmental elements that can influence the operation of a resonator at its resonant frequency, while providing cost-efficient, reliable, repeatable and accurate results. In some embodiments of the invention, the resonance shift detection system includes systems and methods that avoid the complications created by a pair of resonators that are not identically matched by operating each resonator at its own, potentially unique, resonant frequency. By operating each resonator at or near its ideal resonance, the benefits of increased sensitivity can be realized. This in turn, provides for faster and more accurate testing.

In some embodiments, multiple sensor-mounted resonators are separately, or individually, driven at different resonant frequencies. Further, a separate phase or frequency offset measurement is performed for each resonator. Each offset is then compared to the other resonators' phase or frequency offsets. In another embodiment the phase or frequency offset is measured relative to the driving signal provided to each respective resonator and not relative to the other resonators' phase or frequency offsets.

In some embodiments, a sensor for resonance shift detection of chemical and/or biological materials includes one or more printed circuit boards, with one or more resonator dies mounted thereon. The resonator dies in one example embodiment are bulk acoustic wave (BAW) devices. The close proximity of two or more resonators ensures that the resonators are subjected to substantially identical environmental conditions during a material sensing operation. The use of sensor/reference pairs in which one resonator is a sensor and the other resonator is a reference resonator, effectively allows accurate resonance shift measurements and cancellation of environmental effects during material sensing operations using the sensing assembly.

According to various implementations, the sensors for resonance shift detection can include back-to-back PCB configurations utilizing two substantially different PCBs. In one approach, the resonator on one PCB is situated off-center while the resonator on the other PCB is centered. In this configuration, the reference and sensing resonators can still have sufficient distance there-between to reduce cross talk between the two resonators. In another aspect of the present invention, the resonators on the two PCBs are constructed such that the back-to-back PCB configuration results in the reference and sensing resonators being directly opposed.

In some embodiments, the sensing resonator is coated with a different material than a reference resonator depending upon the material to be detected. By varying the coating on the resonators, the resonance shift detection system allows universal use for various diagnostic testing of chemical and/or biological materials without changing any of the other system structural components. Sensors for resonance shift detection of chemical and/or biological materials effectively allow fast response times for the detection of the respective chemical and/or biological material, in the field detection capabilities, small sample sizes, minimally trained individuals, low direct and indirect costs, and electronically transmittable data.

In some embodiments, the resonance detection system includes an on-board power source, such as a battery, super capacitor, solar-power arrangement or any combination thereof, for powering the electronic instrument, and an easily mounted disposable sensor that may be contained within a sensor housing assembly. The sensor has a biological coating that specifically binds with the desired target molecule and provides the mechanism of detection and quantification. A specimen (whole blood, urine, saliva, or any other liquid) is drawn into the sensor housing assembly and brought into contact with the resonators of the sensor, which may or may not be a single-use sensor, within the sensor housing assembly. Electrical measurements of the sensor (i.e. a change in phase or resonant frequency of the RF wave) indicate if the target is present, and if present, its concentration. For each analysis, a new sensor is attached to the instrument.

In some embodiments, the tuning of the sensor can be performed to determine the exact resonant frequency of the resonator prior to the material sensing operation. This tuning can account for the various electrical properties associated with the sensors' physical connection to an instrument as well as the immediate environmental conditions. A second tuning can also optionally be performed in situ promptly after the sensor is introduced into a specimen for sensing.

In general, the rate of change of the resonance characteristics varies with the concentration of the target. The rate of change of the resonance characteristics for the most concentrated sample occurs faster than the lowest concentrated sample. The binding kinetics, such as, for instance, the slope of the response of known samples, or a total magnitude of a change in the response to introduction of the sample as a function of time, can then be used to generate a calibration curve so that the concentration of unknown samples can be determined by interpolation of the sensor response against the curve. During manufacturing, sensors may be factory calibrated by production lot, allowing the user easy determination of the concentration of an unknown sample without further calibration.

Still another aspect of the invention is directed to fast in-situ sensor tuning, which allows the driving signal frequency to be determined very quickly from the time a sensor is exposed to the sample under test.

In another aspect of the invention, a resonating sensor system is configured to deliver accurate test results even with direct introduction of unrefined sample onto a resonating sensor's surface. The biosensor generates a real-time electrical output signal proportional to the binding of analyte onto the sensor's surface. The rate of analyte binding, referred to as binding kinetics, is proportional to the concentration of analyte in the unrefined sample. In this aspect, the introduction of the sample to the surface of the resonating sensor is automatically detected as a step change in the sensor's resonance characteristics. By very rapidly initiating measurement in response to the detection of the sample introduction, the initial on rate of the binding kinetics can be measured. Likewise, for total change measurement, having a precise starting point corresponding to actual introduction of the sample to the sensor facilitates accurate measurement of the binding kinetics.

In a related aspect of the invention, as applied to systems utilizing driving signals having a set frequency such as phase shift detection systems, in order for the biosensor system to deliver accurate test results, a fast tuning is be performed at the initial time that the unrefined sample is presented to the sensor. Some of the embodiments described below accomplish this with an initial air tuning prior to sample introduction, nearly instantaneous electronic detection of sample presentation to sensor's surface, followed by fast tuning performed in the presence of the sample to be analyzed.

Figure 1B:
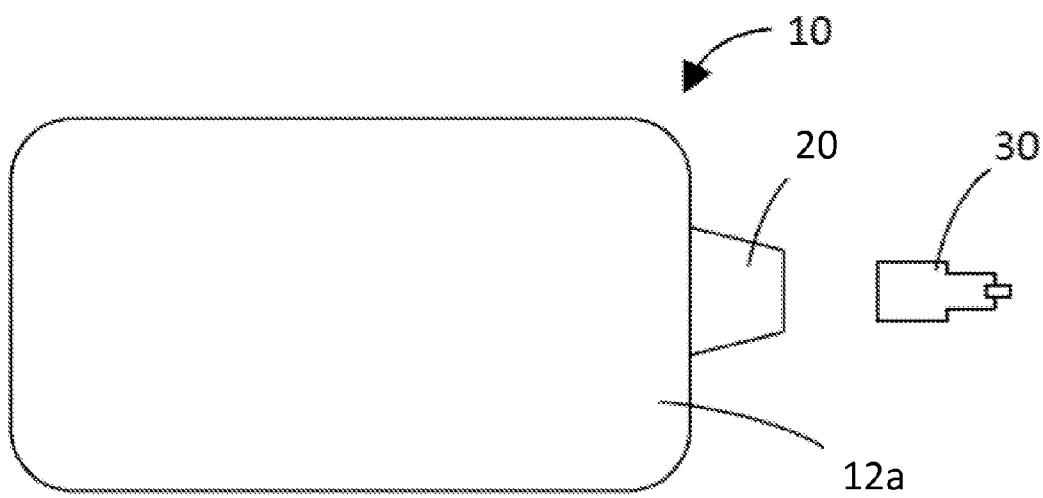
FIG. 1B is a diagram illustrating the hand-held resonance shift detector system of FIG. 1A with the sensor detached from the interconnector and the interconnector attached from the instrument.

Turning now to the drawings, the components of the resonance shift detector system according to some embodiments of the present invention are illustrated. In some embodiments, the resonance shift detector system can be relatively small in size to be portable such that it can be utilized in the field for specific diagnostic testing applications. In some other embodiments, the resonance shift detector system can be configured for diagnostic testing in a laboratory setting. As shown in FIGS. 1A and 1B resonance shift detector system 10 is illustrated in a hand-held or portable configuration that includes an instrument 12a capable of being interfaced with a sensor assembly 30 by an interconnector 20, which can be used for point of need diagnostic testing in the field.

Figure 2:
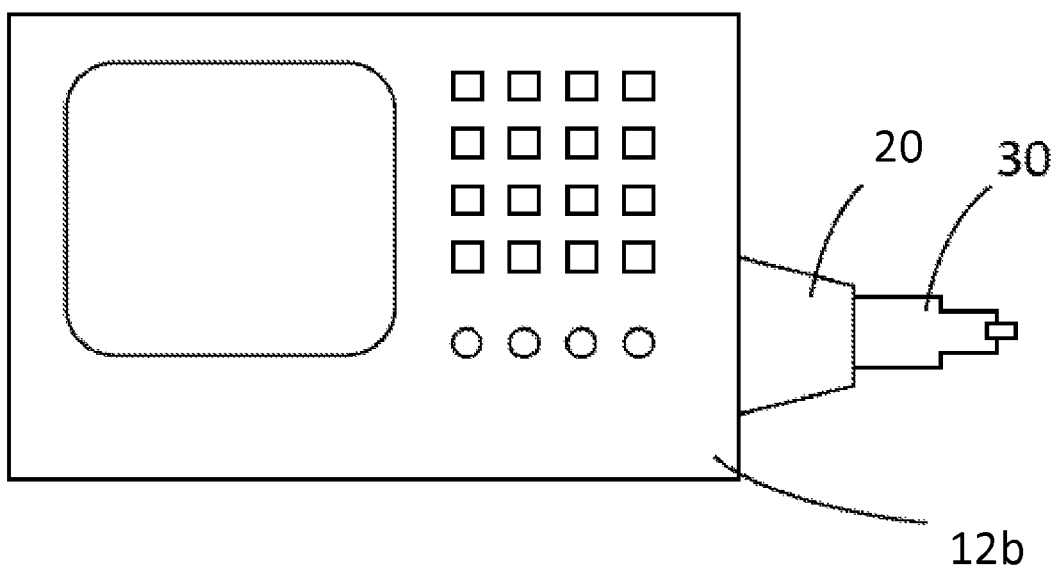
FIG. 2 is a diagram illustrating a laboratory bench resonance shift detector system according to one embodiment.

As illustrated in FIG. 2, the resonance shift detector system is illustrated in a laboratory bench or more permanent configuration that includes an instrument 12b, such as a Network Analyzer, capable of being interfaced with a sensor assembly 30 by an interconnector 20. The sensor assembly 30 mounted on an interconnector 20 and coupled to a laboratory-bench instrument 12b, such as a Network Analyzer, allows diagnostic testing in a laboratory setting, quality control testing of a batch of sensors during production, and/or the development of coatings on the sensor assembly 30 for target material diagnostic testing. The instrument including, but not limited to hand-held instrument 12a and laboratory-bench instrument 12b, may have means for connection to the internet or otherwise transferring information, such as one or more USB ports, wireless connection, or the like.

In some embodiments, the interconnector 20 can contain a data storage device such as a ROM or flash EEPROM. The data storage device may serve to set up the instrument for specific market applications by including software or identification information that allows the instrument to understand the particular use of the resonance shift detector system 10 as it relates to the sensor assembly 30. For instance, the read-only memory may contain basic information or algorithmic instructions for the interpretive logic of the instrument that relates to the output signal of the sensor assembly 30, which may serve to limit the resonance shift detector system 10 to specific applications, such as limited only to use in one of: veterinary applications, toxicology applications; drugs of abuse applications; GMO grain applications, for example.

The data storage device can also contain sensor-type specific information such as the general frequency range or approximate resonance frequency of the resonator as determined during post-production testing. This information could, for example, reduce sensor detection and calibration setup time when a new sensor is coupled to an instrument. In a related embodiment, the data storage device contains lookup tables of calibration correction constants that are indexed by lookup codes individually determined for the sensors at the factory. In various other embodiments, the lookup code may be supplied via printed label, barcode label, or using a RFID tag.

In another related embodiment, the sensor includes a read-only memory (ROM) or small flash device having its own specific calibration constants specific to the individual sensor assembly 30. This data could be supplied based on factory calibration performed on a representative sample taken from the manufactured lot in which the individual sensor assembly 30 was fabricated. In yet another embodiment, the instrument is configured with a network interface device and associated firmware/drivers, which enable the device to automatically initiate a query over a network to obtain calibration constants for the specific sensor. This embodiment eliminates the need for maintaining calibration data locally. Instead, when a new sensor is attached, the instrument determines the serial number associated with the particular sensor (using RFID, bar code scanning, etc.), and uses that information to form its query. The database having specific sensor calibration data may be stored on a server located at the laboratory facility, or remotely (e.g., at the manufacturer's facility), in which case the network over which the query is placed is a wide area network (WAN) such as the Internet.

Sensor assembly 30 includes one or more resonators such as bulk acoustic wave devices, for instance, described in greater detail below. In various embodiments, sensor assembly 30 may or may not include circuitry that interfaces with the one or more resonators. For instance, in one type of embodiment, actuation circuitry that causes the one or more resonators to oscillate, is incorporated into the sensor assembly 30. In another embodiment of this type, measurement circuitry, including analog-to-digital conversion, is incorporated into sensor assembly 30. In another type of embodiment, the actuation and measurement circuitry is located in the housing of instrument 12a or 12b.

Figure 3:
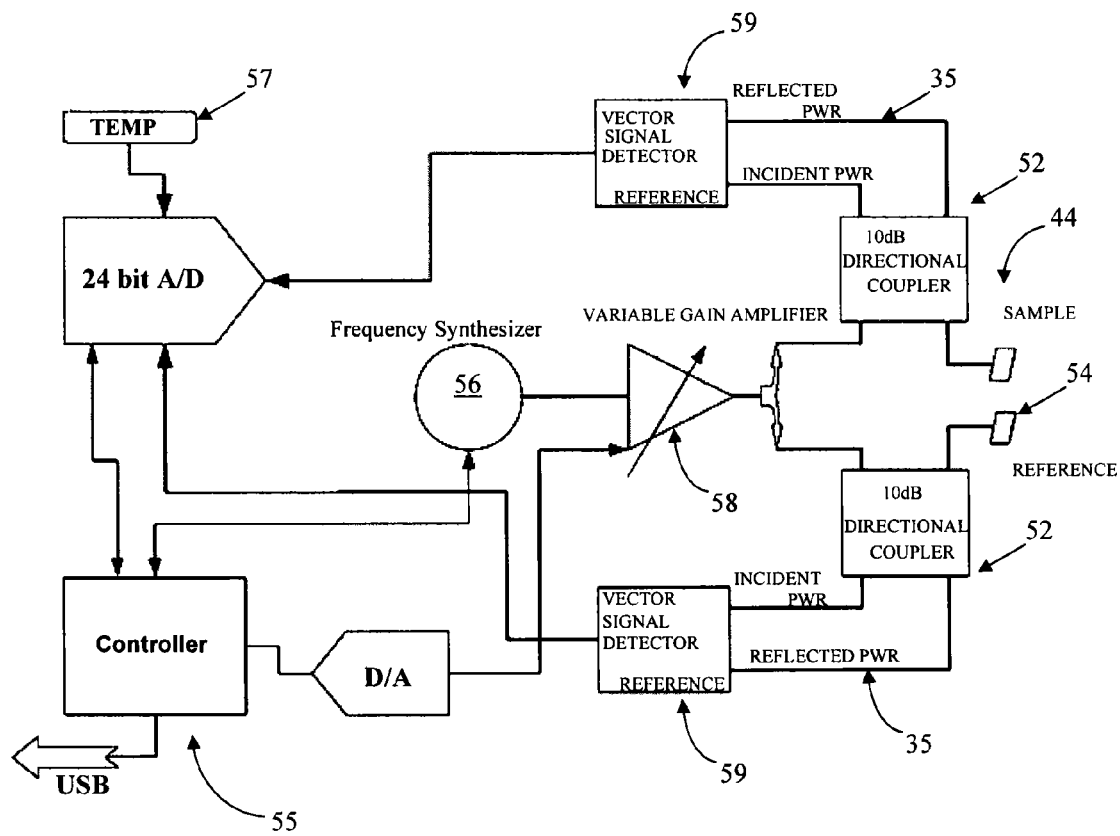
FIG. 3 is a block diagram view of an exemplary implementation of a resonance shift detector system that uses phase shift detection according to one embodiment.

In one embodiment of the invention, as depicted in FIG. 3, a system that detects resonant characteristics changes of a sensing resonator and a reference resonator. In this example embodiment, the phase angle of each resonator is the resonant characteristic that is being monitored.

A sample resonator 44 and reference resonator 54 are each coupled to separate directional couplers 52. The directional couplers 52 provide their respective resonators 44, 54 with a signal generated by a microcontroller 55 controlled frequency synthesizer 56 and a variable gain amplifier 58. The directional couplers 52 also each output the incident signal and the reflected sensor signal 35 to a vector signal detector 59. The vector signal detector 59 for each resonator processes the signals to produce an output signal indicative of a phase difference between the input and output frequency signals. These signals are delivered to an analog to digital converter and then read by the microcontroller 55.

In various embodiments, microcontroller 55 uses the output signal for either one, or both, of the sensing and reference resonator to detect an abrupt change indicative of introduction of the sample to the resonators, as will be described in greater detail below.

Additionally, microcontroller 55 is programmed to compare any difference in phase change, or the rate of phase change over time, between the incident signal and the reflected sensor signal 35 of both the sample and reference resonators. Because the change in phase of the sample resonator 44 is caused mainly by the binding of the material being detected on the surface of the sensing resonator, a greater phase change over time will be observed in comparison to any phase change over time, due to environmental effects, observed at the reference resonator. Because of the potential effect temperature can have on the resonant frequency of the resonators, a temperature sensor 57 can be included to provide temperature data to microcontroller 55.

According to one aspect of the present invention, separate sensing and reference resonators are independently driven at their own unique individual resonant frequencies, which are separately determined. The use of distinct driving frequencies provides improved sensitivity since the sensor and reference resonators are operated their respective exact resonance frequencies (or as close to them as feasible in a given system), and any changes to the resonant frequency is more easily discernable.

Figure 4:
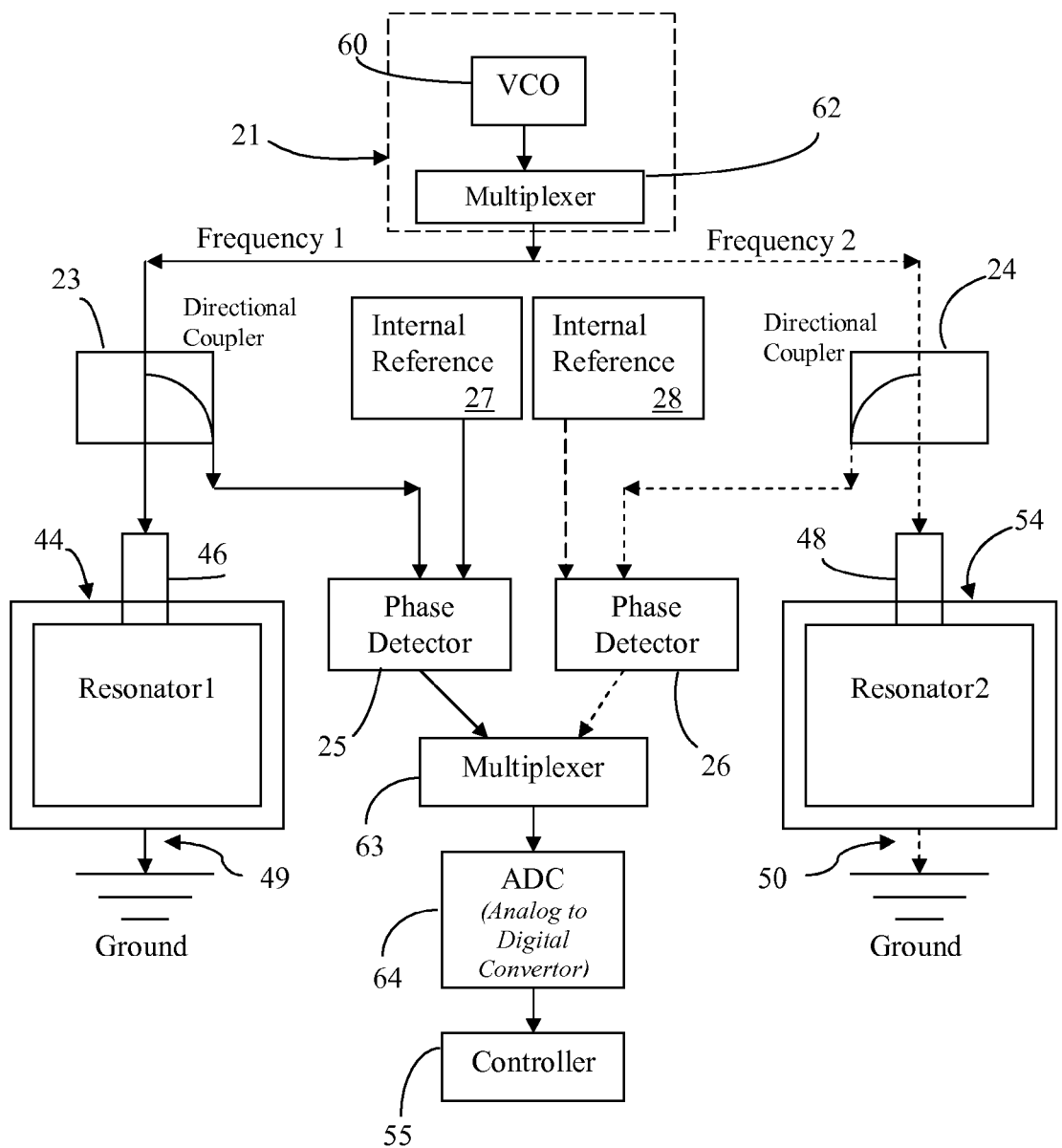
FIG. 4 is a block diagram view of an exemplary implementation of a resonance shift detector system that uses phase shift detection utilizing a one-port sensing resonator and a one-port reference resonator according to one embodiment.

FIG. 4 illustrates an example measurement arrangement according to one embodiment, using a one-port sensing resonator 44 and a one-port reference resonator 54, each of which receives its own separate driving signal. A one-port resonator has an electrode 46, 48 that is used for both signal input and output. The other electrode 49, 50 of each one-port resonator is typically grounded.

This embodiment includes a signal source 21, which includes a voltage-controlled oscillator 60 and a multiplexer 62, provides an input signal of a first frequency which is at or near the resonant bands of the first resonator's resonant frequency. Signal source 21 also provides an input signal of a second frequency which is at or near the resonant bands of the second resonator's resonant frequency. In a variation of the arrangement illustrated in FIG. 4, a separate oscillator, such as an additional VCO (not shown) can provide an input signal of a frequency for each of the respective resonators, which could eliminate the need for multiplexer 62.

The input signal provided by the signal source 21 is directed by directional couplers 23, 24 to their respective sensing and reference resonators 44, 54. The reflected output signals of the resonators 44, 54 are directed to the phase detectors 25, 26 by the respective couplers 23, 24. Each of the phase detectors 25, 26 additionally receives a reference signal from a corresponding internal reference signal generator 27, 28. Phase detectors 25 and 26 process the sensor and reference signals to produce output signals indicative of a phase difference between the input and output frequency signals of their respective resonators. The output of phase detectors 25,26 is selected via multiplexer 63 (which operates generally synchronously with multiplexer 62—both may be implemented in a single package with a common control input, or may be separate devices, each with its own control input), and converted to a digital representation by analog-to-digital converter (ADC) 64, which is interfaced with controller 55.

Controller 55 is programmed to apply logic to interpret the output signals. Introduction of the sample to the resonators generally causes a common abrupt change to both, the sensing and reference resonators' output signals, which controller 55 is programmed to detect. The binding of the material being detected on the surface of the sensing resonator 44 generally causes a change of phase angle $d\Phi/dt$ between the sensing resonator and reference resonator when the detected material is present.

The phase detectors 25, 26 in the illustrated embodiment can include a double-balanced mixer (or a mathematic multiplier) which receives the sensor and reference signals. The output of the mixer is passed through a low-pass filter which eliminates a time dependent term and leaves only the DC term as the output of the phase detector 25. As provided in more detail in U.S. Pat. No. 5,932,953, the disclosure of which is incorporated by reference herein, the resulting measured phase shift change can be used to derive the total amount of the material bound on the surface of the sensing resonator 44. In some embodiments, the signal source 21 generates an analog signal and the phase detector 25 generates either an analog or a digital output signal after receiving the signal and reference signals and processing the information there from.

In the embodiment illustrated, the signal from each respective resonator 44, 54 is directed to a separate respective phase detector 25, 26 each respective phase detector 25, 26 processing the respective sensor or reference signal to produce a phase signal indicative of a phase shift. The phase shift data is converted to digital data that can then compared to each other, or to their respective source frequencies, by the controller 55 to determine the net difference in phase shift between the sensing and reference resonators. The different phase shift being caused by the binding of the material being detected on the surface of the sensing resonator 44 and not on reference resonator 54. Controller 55 can be configured to periodically sample the output of phase detectors 25, 26 or any other appropriate mechanism for observing and recording the change in phase of the two signals during operation.

The sensing resonator 44 is coated with a test reagent that binds to or captures the analyte to be detected during the diagnostic testing. The reference resonator 54 is coated with a reference reagent that does not bind with or otherwise capture the analyte during the diagnostic testing.

Figure 5:
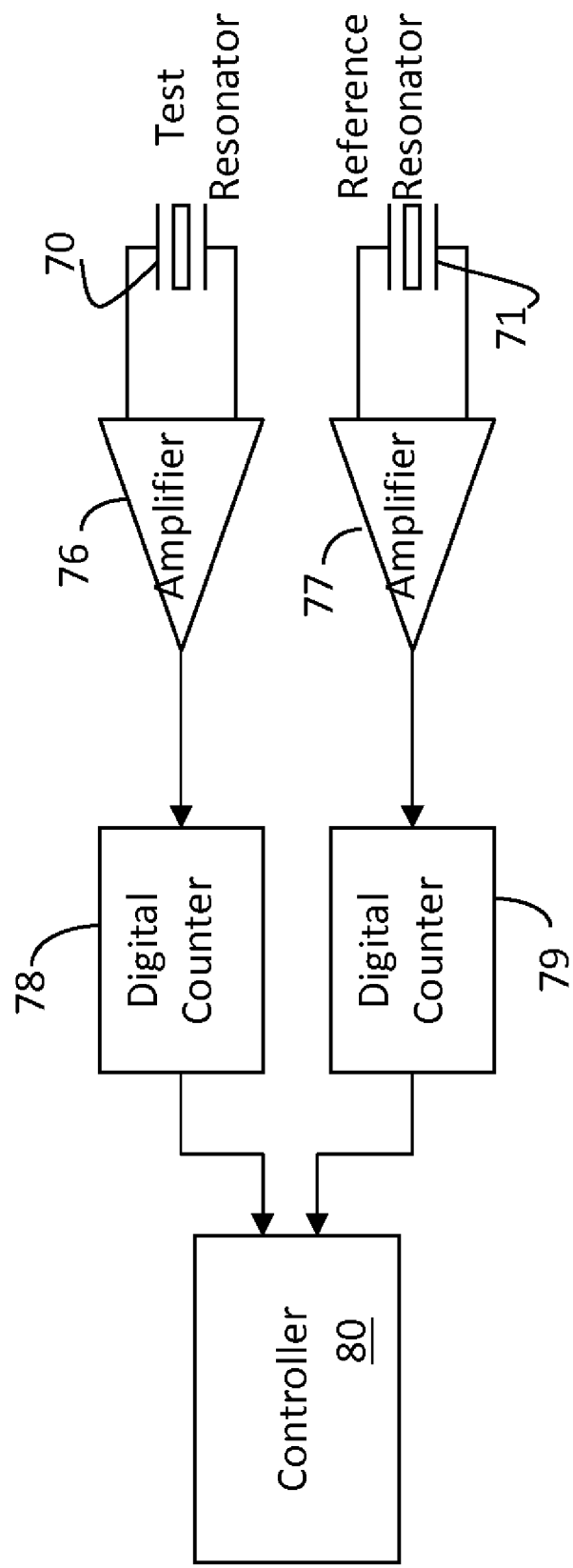
FIG. 5 is a block diagram illustrating an exemplary implementation of a resonance shift detector system that uses frequency shift detection according to one embodiment.

FIG. 5 is a block diagram illustrating a measurement arrangement with a test and reference resonator according to another embodiment in which a frequency shift detection scheme is used to detect a change in resonance. Test resonator 70 and reference resonator 71 are connected respectively to amplifiers 76 and 77 as shown. Amplifiers 76, 77 are constructed such that, when operated with resonators 70, 71, they generate output signals at the resonant frequency of resonators 70, 71. Thus, changes in the resonant frequency of test resonator 70 or reference resonator 71 (such as those induced by the capture of analyte on the surface of the test resonator, or by localized environmental changes in the sample solution in which the test and reference resonators 70, 71 are immersed) will cause changes in the resonant frequency delivered from amplifiers 76, 77 to digital counters 78, 79.

The resonant frequencies are generated by amplifiers 76 and 77, and passed to digital frequency counters 78 and 79, the outputs of which are interfaced with controller 80. Controller 80 thus has a continuous reading of each resonant frequency, the changes in which represent changes in the resonance of test resonator 70 and reference resonator 71. As will be described in greater detail below, in one embodiment, controller 80 is programmed to detect an abrupt change in resonance characteristic of either one, or both, the sensing and reference resonator, as an indicator of introduction of the sample. Controller 80 is further programmed to ascertain differences in the changes of resonance characteristics between test resonator 70 and reference resonator 71, along with the rate of change in resonance of this difference. From this information, controller 80 is programmed to determine whether the test resonator 70 has experienced binding of analyte and, from the rate of change in its resonance characteristic (relative to that of the reference resonator 71), to determine the concentration of analyte in the sample fluid.

During the sampling process, the sensor assembly 30 is introduced into a liquid or gaseous sample, or the sample aliquot may be introduced to the sensing and reference resonators 44, 54 by way of a sensor housing assembly. The liquid sample for the diagnostic test may include blood, urine, serum, saliva, water, or any other liquid sample that may be of interest. As soon as the sample contacts the sensing and reference resonators 44, 54, there is a change in signal from the resonators 44, 54. The instrument 12 is waiting to receive the change in signal, and once the change in signal is detected, the instrument 12 begins the interpretative sequence of collecting data. The instrument 12 continues to collect data until either (i) the instrument 12 times out because the signal has not changed, or (ii) depending upon the speed with which the signal changes, the instrument 12 will stop collecting data once enough data is received to give an interpretation of the diagnostic test. An interpretation of the diagnostic test may include an indication that the target material, or analyte, has been bound or captured onto the sensing resonator and a quantification of the target material.

Figure 6A:
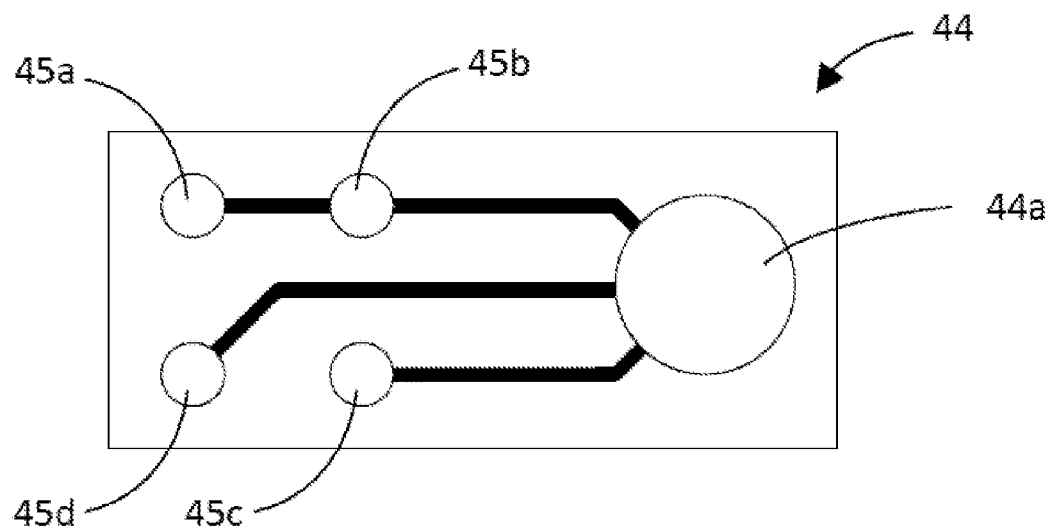
FIG. 6A is a schematic top view of a resonator assembly according to one embodiment.
Figure 6B:
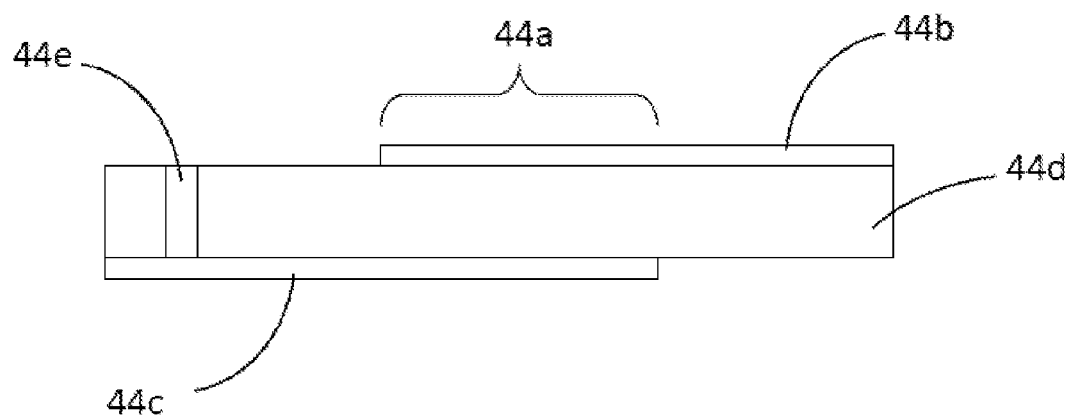
FIG. 6B is a schematic of a partial layer view of the resonator assembly of FIG. 6A.

Referring now to FIG. 6A the top surface of an example resonator assembly is illustrated, which represents the sensing resonator assembly and reference resonator assembly. For ease of reference, the following description refers to the sensing resonator assembly 44, although the description is equally applicable to the reference resonator assembly 54. The top surface of the sensing resonator assembly 44 contains a set of solder bumps 45a-45d. Solder bumps 45a-45c are connected to ground within the resonator assembly 44. Solder bump 45d is connected to the resonator 45A by way of a via through the piezoelectric layer and a resonator conductor between, which is further illustrated by the partial layer view in FIG. 6B. The resonator assembly 44 is also cantilevered over the edge of the printed circuit board to allow the resonator 45A to be exposed to the surrounding environment during the testing process. In some embodiments, the solder pads may be on a different side of the resonator assembly 44 than the resonator 45A, such that the resonator assembly 44 does not necessarily have a cantilevered configuration. In yet other embodiments, the PCB may be configured such that the resonator assembly is mounted in a depression in the PCB and the electrical connection between the resonator assembly and PCB is accomplished with a conductor such as a conducting epoxy.

In the construction of resonators, the relative surface area of the resonator 44A is directly related to the frequency at which the resonator resonates, with higher frequency resonators having a smaller surface area and lower frequency resonators having a larger surface area. For example, a smaller-sized resonator (e.g. diameter of 154.4 µm) has a resonant frequency of 2.25 GHz while a larger-sized resonator (diameter of 254 µm) has a resonant frequency of 900 MHz. Accordingly, it is contemplated that resonators with various resonant frequencies may be used depending upon the desired resonant frequency and any regulatory restrictions on the frequencies available to be used. The thickness of the piezoelectric layer also affects frequency with a thinner piezoelectric resonating at a higher frequency than a thicker layer. As discussed previously, while various resonators of similar size have generally similar resonant frequencies the slight variation in size, potentially due to variances in manufacturing, can result in similar resonators with close but meaningfully different resonant frequencies.

In some embodiments, a back-to-back paddle configuration allows the sensing resonator 44 and the reference resonator 54 to be located in a close proximity with each other, the two resonators are subjected to substantially identical environmental conditions during a material sensing operation, which allows for accurate resonance shift measurements and effective cancellation of the environmental effects. Environmental effects that may be cancelled may be a result of viscosity, pH, temperature, particulates, and any other environment conditions within the sample that will affect the sensing resonator 44 during diagnostic testing.

In another aspect of the invention, multiple sensor/reference resonator pairs are employed. Each sensor/resonator pair may be configured to detect a different material, or multiple ones of sensor/resonator pairs may be used in order to provide redundantly for improved accuracy or reliability of the instrument. In related embodiments, provisions are made to reduce cross-talk between the multiple pairs of sensor/reference resonator pairs.

One approach is to provide physical separation between pairs. Physical separation may be achieved by placing the different sensor/reference resonator pairs on separate substrates to provide mechanical and electrical isolation. Another way of achieving physical separation is by placing the different sensor/reference pairs far enough apart so that any mechanical or electrical coupling is rendered nominal.

Cross-talk between the resonators may also be reduced or eliminated by the pairs of sensor/reference resonator pairs being operated at different frequencies. For example, two or more pairs of resonators mounted on a single PCB can be fabricated to have their nominal resonant frequencies spaced apart by an amount sufficient to reduce any cross-talk to a negligible level. The spectral spacing sufficient to achieve the isolation depends on a variety of factors, such as the quality factor of the oscillation which, in turn, depends on the materials, construction, and geometry of the resonators themselves; additionally, the required spectral spacing to reduce crosstalk to an acceptable level can depend on the selectivity of the measuring circuitry. The frequency separation can be defined in terms of percentage of driving frequency. For instance, the separation can be about 1-5% of driving frequency. Thus, in embodiments where the resonant frequency is in the range of 750-1000 MHz, the frequency separation may be approximately 15 MHz between the multiple sensor/reference resonator pairs.

Figure 7:
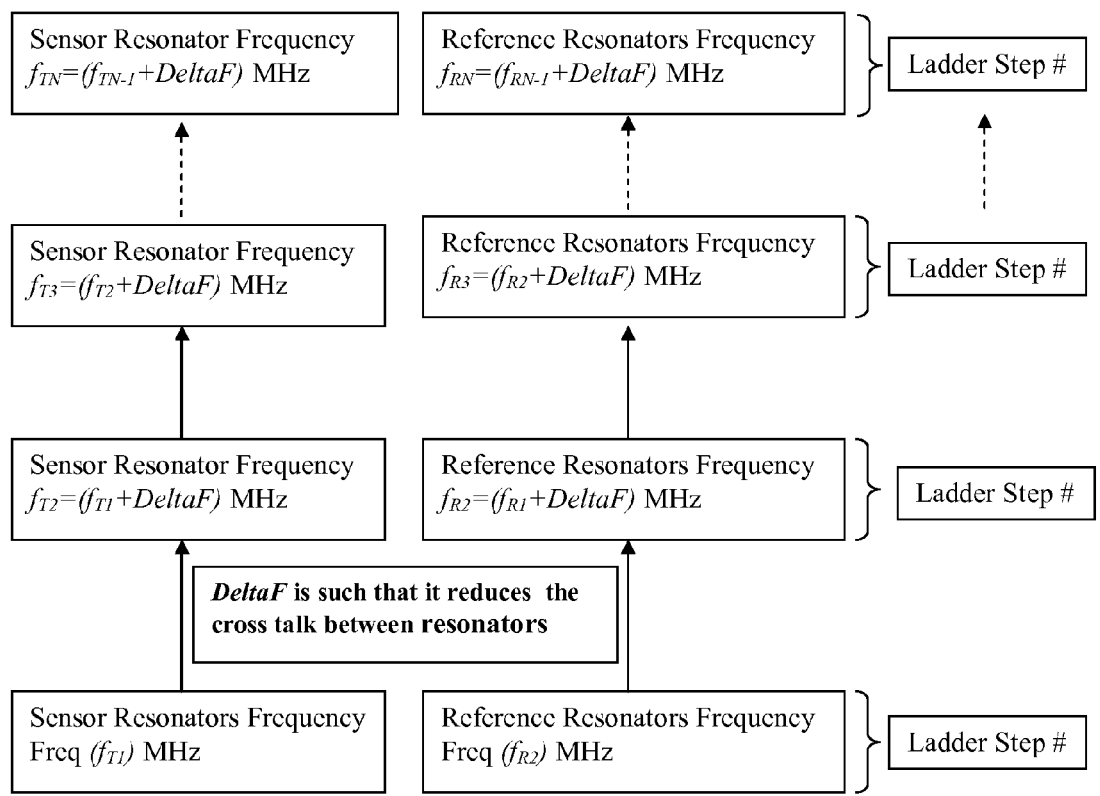
FIG. 7 is a diagram illustrating a frequency ladder approach of determining frequency divisions for operating multiple sensor/reference resonator pairs at non-interfering frequencies in a multiplexed embodiment.

FIG. 7 is a diagram illustrating a process of determining resonant frequencies for different pairs of resonator on a multi-resonator board according to one embodiment. The approach of this embodiment uses a fixed frequency (DeltaF) Ladder design. In a multiplexed design of a resonator group, the frequency difference (DeltaF) between any two resonators at the adjacent ladder steps is such that it reduces the cross talk between the resonators to a negligible amount. The frequency difference between the adjacent ladder steps can be fixed or may be variable and is defined by the application or test. As depicted in FIG. 7, each sensor/reference resonator pair is operated at a similar frequency. However, other sensor/reference resonator pairs are each operated at a frequency difference DeltaF.

In another type of embodiment, groups of more than two sensors may be utilized in a measurement arrangement. Rather than being arranged in pairs, groups may be composed on three or more sensors, of which there is more than one sensing resonator, and/or more than one reference resonator. In one type of configuration, a group of resonators is arranged in close proximity so that the group can be exposed to the same test environment. One such group of sensors can include a total of eight resonators, of which seven are sensors, and one is a reference. As a variation of this example, embodiment, a different group of eight resonators includes six sensors and two reference resonators.

In operation, for each group of resonators, the resonance shift of each sensing resonator can each be compared against a certain individual reference resonator. Alternatively, an average (or other statistically aggregated) resonance shift of more than one sensor can be compared with an average (or otherwise aggregated) resonance shift of more than one reference resonator of the group. In various instruments implementing aspects of the invention, a variety of different measurement arrangements using groups of more than two sensor/reference resonators can be employed in order to achieve improved accuracy or precision, or to provide a more comprehensive test which can detect a plurality of different materials in the sample under test.

Various embodiments, including one or more resonators mounted on a plurality of connected printed circuit boards, are also contemplated. One such embodiment includes a sensor with multiple PCB layers, each layer or sub-group of layers including one or more resonators mounted in a staggered or grid layout across the multiple PCB layers, each resonator having the same axis of resonance. In other embodiments, multiple individual sensors with one or more resonators are constructed in any of various configurations including, but not limited to a cross, diamond, triangle, square, pentagonal or circular orientations formed from three or more stacked PCB layers. An appropriate interconnector can be employed to couple the plurality of PCB layers to an instrument configured to operate a multi-resonator sensor.

Figure 8A:
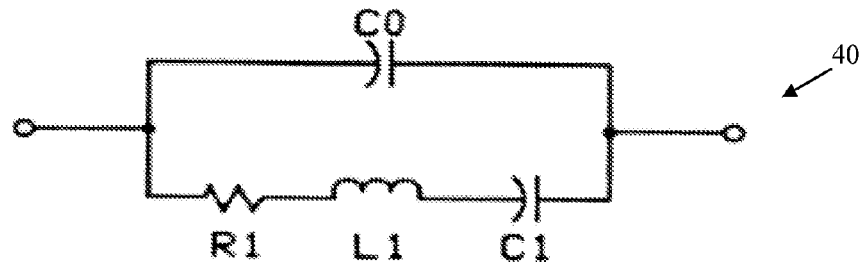
FIG. 8A is a schematic diagram illustrating a simplified model of a resonator in the resonance shift detector system according to one embodiment.

FIG. 8A is a circuit diagram illustrating a simplified resonator sensor model 40. The model 40 provides a link between the physical property of the resonator crystal and the oscillator. The physical constants of the crystal determine the equivalent values of R1, C1, L1 and C0 of the device. Resistance (R1) is a result of bulk losses, C1 is the motional capacitance, L1 is the motion inductance as determined by the mass, and static capacitance (C0) is made up of the electrodes, the holder, and the leads. When operated far off resonance the structure is simply a capacitor with capacitance C0, but at the precise resonant frequency of the crystal the circuit becomes a capacitor and resistor in parallel. The reactance of the crystal approaches zero at the point of series resonance and reaches a maximum at the anti-resonant frequency fA.

One example of determining the various properties of the resonator is a lumped element method including the following steps performed on data gathered in a SnP 1-port data file:
1) Convert $s11(f)$ to $z11(f)$ for all frequency measured.
2) The real($z11$) at the highest frequency (fh) is the contact resistance $Rc=\text{real}(z11(fh))$.
3) The stray capacitance Co is also computed at the highest frequency (fh)

$$Co=1/[2*pi*fh(hz)*\text{imag}(z11(fh))]$$

Figure 8B:
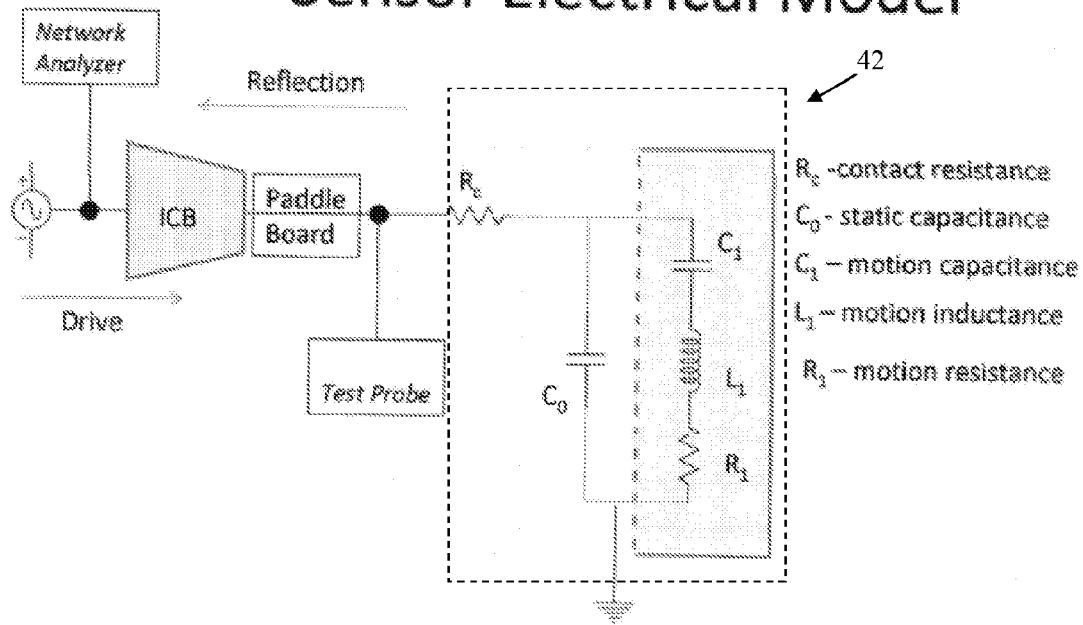
FIG. 8B is a schematic diagram illustrating a more detailed model of a resonator sensor in the resonance shift detector system according to one embodiment.

4) Remove the effects of Rc by subtracting it from z11. $z11'(f)=z11(f)-Rc$
5) Series resonant frequency fs can be determined when the sign of Imag[$z11''(f)$] changes neg to pos.
6) Motional inductance is computed as $$Ls=(1/(4*pi))*(\text{imag}[z11''(fs)]-\text{imag}[z11''(fs-\Delta f)])/\Delta f$$
where $\Delta f=500$ kHz 7) Motional resistance is $Rs=\text{real}[z11''(fs)]$
8) Motional capacitance is $Cs=1/[(2*pi*fs)^2*Ls]$ FIG. 8B is a diagram illustrating a more sophisticated resonator model 42 that includes contact resistance (Rc). Both the contact resistance Rc and the static capacitance C0 are important variables that should be de-embedded in order to observe the changes happening on the resonator surface. As will be understood by those skilled in the art, the interconnector 20 may also introduce a translation and rotation effect on the measurements of the resonator sensors. Because the act of mounting a crystal on a sensor can affect the contact resistance Rc and the static capacitance C0 of the resonator it is important that these parameters be accounted for in the calibration, tuning, and use of the resonator sensors.

One example method of determining the various properties of the resonator with C0 removed includes the following steps:
1) Convert $s11(f)$ to $z11(f)$ for all frequency measured.
2) The real($z11$) at the highest frequency (fh) is the contact resistance $Rc=\text{real}(z11(fh))$.
3) The stray capacitance Co is also computed at the highest frequency (fh)

$$Co=1/[2*pi*fh(hz)*\text{imag}(z11(fh))]$$

4) Remove the effects of Rc by subtracting it from z11. $z11'(f)=z11(f)-Rc$
5) Remove the effects of Co by removing it from $$y11'(f) \text{ or } z11''(f)=1/[(1/z11'(f))-j(2*pi*f*Co)]$$

6) Series resonant frequency fs can be determined when the sign of Imag[$z11''(f)$] changes from neg to pos.
7) Motional inductance is computed as $$Ls=(1/(4*pi))*(\text{imag}[z11''(fs)]-\text{imag}[z11''(fs-\Delta)])/\Delta f$$
where $\Delta f=500$ kHz 8) Motional resistance is $Rs=\text{real}[z11''(fs)]$
9) Motional capacitance is $Cs=1/[(2*pi*fs)^2*Ls]$ The above steps can in a third example be modified to result in the following method of modeling a resonator:
1) Convert $s11(f)$ to $z11(f)$ for all frequency measured.
2) The real ($z11$) at the highest frequency (fh) is the contact resistance $$Rc=\text{real}(z11(fh)).$$

3) The stray capacitance Co is also computed at the highest frequency (fh), $$Co=1/[2*pi*fh(hz)*\text{imag}(z11(fh))]$$

4) Remove the effects of Rc by subtracting it from z11.

$$z11'(f)=z11(f)-Rc$$

5) Motional inductance is computed as $$Ls=(1/(4*pi))*(\text{imag}[z11'(fs)]-\text{imag}[z11'(fs-\Delta f)])/\Delta f=500 \text{ kHz}$$

6) Motional resistance is $Rs=\text{real}[z11'(fs)]$
7) Motional capacitance is $Cs=1/[(2*pi*fs)^2*Ls]$ The resonator models can be utilized to screen manufactured resonators in order to evaluate and select appropriate resonators.

In one embodiment, the following method can be used to evaluate resonators:
1) Load S1p files for all resonators.
2) Convert $s11(f)$ to $Z11(f)$ for all frequencies measured.
3) Compute Contact Resistance at highest frequency (fh)

$$Rc=\text{real}(z11(fh))$$

4) Remove the effects of Rc by subtracting it from z11.

$$z11'(f)=z11(f)-Rc$$

5) Compute stray capacitance C0 at highest frequency (fh).

$$C0=1/[2*pi*fh(hz)*\text{imag}(z11(fh))]$$

6) Compute Motional Inductance $$Ls=(1/(4*pi))*(\text{imag}[z11(fs)]-\text{imag}[z11(fs-\Delta f)])/\Delta f$$

7) Compute Motional Resistance $$Rs=\text{real}[z11'(fs)]$$

8) Compute Motional Capacitance $$Cs=1/[(2*pi*fs)^2*Ls]$$

9) Compute Q values $$Q=1./(2*pi*Fs*C1*(Rs+Rc))$$

Next a Variable Standard Deviation Method can be employed to narrow the selection of resonators.
  10) Find resonators that have Series Resonance defined
  11) Find resonators having Q values >80
  12) Find the subpopulation of resonators that have passed both steps 10 AND 11.
  13) Compute the mean and Standard Deviation of Resonance frequencies measured from subpopulation of resonators from step 12
  14) Compute the mean and Standard Deviation of resonators calculated Contact Resistance from subpopulation of resonators from step 12
  15) Compute the mean and Standard Deviation of resonators calculated Motional Resistance from subpopulation of resonators from step 12
  16) Compute the mean and Standard Deviation of resonators calculated Motional Inductance from subpopulation of resonators from step 12
  17) Compute the mean and Standard Deviation of resonators calculated Motional Capacitance from subpopulation of resonators from step 12
  18) Compute the mean and Standard Deviation of resonators calculated Static Capacitance from subpopulation of resonators from step 12

Once the mean and standard deviation are calculated as described a boundary condition on each parameter is applied according to the following steps performed on the subpopulation of resonators from step 12:
  19) Compute the distribution of Contact Resistance
  20) Compute the distribution of Motional Resistance
  21) Compute the distribution of Motional Inductance
  22) Compute the distribution of Motional Capacitance
  23) Compute the distribution of Static Capacitance
  24) Select varying SD value for each variable from steps 19-23
  25) Find the subset of resonators that pass all user selected SD boundary conditions in step 24
  26) Compute the yield and visually inspect smith chart circles for any outlying resonators
  27) Tweak SD values for each variable in step 24 until all undesirable resonators are excluded from the subpopulation.

One example implementation of the process of calculating Q values is realized in the following code:

```
Ref_Coeff=10.^(MA./20);
  RE=Ref_Coeff.*cos(PA.*pi/180);
  IM=Ref_Coeff.*sin(PA.*pi/180);
  Admittance=(.02*(1-RE-j*IM)./(1+RE+j*IM));
  Real_Adm=real (Admittance);
  Imag_Adm=imag (Admittance);
    DEN=1-(2*RE) + (RE.*RE) + (IM.*IM);
    REZ = (50*(1-(RE.*RE) - (IM.*IM)))./DEN;
    IMZ = (50*2*IM)./DEN;
    for L = 1:1:length(RE(1,:))
```

-continued

```
      QMAX = 0;
      for I = 1:length(Freq)
        if (I>=6)
          A=((2*Freq(I)) / (Freq (5) - Freq (1)));
          B=(REZ(I-5,L) * IMZ (I,L)) - (REZ(I,L)*IMZ
          (I - 5,L));
          C=(REZ(I,L) + REZ(I-5,L) ^ 2+(IMZ(I,L) +
          IMZ (I - 5,L))^2;
          Q(I,L) = A*B/C;
          if (abs(Q(I,L)) >QMAX)
            QMAX = abs(Q(I,L));
            FMAX = Freq(I);
          end
        end
      end
    end
FINALQ=[FINALQ Q];
```

The following process is an example for determining the quality factor of a resonator according to one embodiment:

Step1: Compute Reflection Losses.

$$\text{Ref\_losses}=10^{(Mag/20)};$$

Step2: Compute the Reflections Coefficients

```
RE=Ref_losses.*cos(Phase.*pi/180);
IM=Ref_losses.*sin(Phase.*pi/180);
```

Step3: Compute the Admittance from Reflection Coefficients

```
Admittance=(.02*(1-RE-j*IM)./(1+RE+j*IM));
Real_Adm=real (Admittance);
Imag_Adm=imag (Admittance);
```

Step4: Compute the Real and Imaginary IMP

```
DEN=1-(2*RE)+(RE.*RE)+(IM.*IM);
REZ=(50*(1-(RE.*RE)-(IM.*IM)))./DEN;
IMZ=(50*2*IM)./DEN;
```

Steps: Compute Q for each Frequency and each time point of measurement

```
for L=1:1:length(RE(1,:))
  QMAX = 0;
  for I=1:length(Freq)-1
    if(I>=6)
      A=(2*Freq(I))/(Freq(5) - Freq(1));
      B=(REZ(I-5,L)*IMZ(I,L))-(REZ(I,L)*IMZ(I-5,L));
      C=(REZ(I,L)+REZ(I-5,L))^2+(IMZ(I,L)+IMZ(I-5L))^2;
      Q(I,L) = A*B/C;
      if (abs(Q(I,L)) > QMAX)
        QMAX=abs(Q(I,L));
        FMAX=Freq(I);
      end
    end
  end
end
```

The method above can be further modified with the following equations to improve computation speed:

$$Z = \frac{50*(1+10^{(Mag/20)}*e^{(iPhase)})}{(1-10^{(Mag/20)}*e^{(iPhase)})} \qquad 1$$

2: Scaling Factor:

$$A=(2*Freq)/(Freq(5)-Freq(1))$$

$$Q = A*1.2*\frac{\text{real}(Z)*diff(\text{Imag}(Z))-\text{Imag}(Z)\cdot*diff(\text{Real}(Z))}{\text{Abs}(Z)^{\wedge}2} \qquad 3$$

In the frequency shift detection scheme such as in the embodiment described with reference to FIG. 5, the control circuit automatically adjusts the driving frequency of the sensor and reference resonators to always maintain their resonant point, and the adjustment of the driving frequency is indicative of the change in resonance characteristic. In contrast, the phase shift detection arrangement of the embodiments of FIGS. 3 and 4 involves determining optimal driving frequency for the sensor and reference resonators.

A variety of ways to determine a resonator's optimal operating frequency are contemplated. This process, referred to as tuning, or operating point calibration, is carried out rapidly according to various embodiments. This enables the use of phase shift detection schemes for measuring samples having high concentrations of analyte.

In one approach, the determination of a resonator's operating frequency is found by post-processing of gathered data, in which the group delay of phase for each signal frequency supplied to a resonator is determined, and the operating resonance frequency is defined as the frequency of maximum group delay.

In another approach, the operating resonance frequency of the resonator can be efficiently determined in a calculation using measured actual oscillation characteristics represented by the real and imaginary reflection coefficients. In this approach, a the frequency (f1) is determined at which Real(Z) has its maximum value and the frequency (f2) at which Imaginary(Z) has its maximum value. Using this approach, the operating resonance frequency of the resonator is defined as the mean of f1 and f2. This approach provides improved computational efficiency over previously-used techniques. In turn, the computational efficiency allows faster tuning, which can be extremely important in applications where the material being measured binds quickly to the resonant sensor.

In an example of how this calculation may be applied, a sensor is coupled with the instrument and the instrument immediately tunes the resonator in air by sweeping through frequencies over a broad bandwidth. This initial tuning can be accomplished either by determining the group delay at each frequency and identifying the frequency at which the maximum group delay occurs, or by using the calculation at each frequency and finding the mean of f1 and f2 using the method disclosed above. The in-air operating frequency is then used to define a narrow bandwidth, for example +/−5 MHz, or +/−1 MHz, of each resonator's operating frequency, that will be used for a second tuning step that can be carried out once the resonators are exposed to test sample. The second tuning step is accomplished using the calculation method described for the initial tuning step, above, along with a finer sampling interval than that used to sweep through the frequency window used for the first tuning step while the senor was in air.

In a related embodiment, an adaptive frequency sweep is performed instead of a basic sweep using predetermined sampling intervals. For instance, at each operating frequency during the adaptive sweep, the oscillation characteristics (e.g., Real(Z) and Imaginary(Z)) are measured and compared to the corresponding values at previous or subsequent frequencies. The result of this comparison determines if the direction of the sweep is approaching, or moving away from the resonant point. This approach can produce a faster tuning of the resonator to its resonant frequency since the full sweep can be avoided in some cases.

In various embodiments, the frequency sweeping, calculations, interpretation of measured parameters, and control of the tuning process is carried out by a controller interfaced with the sensing and measuring circuitry and programmed to execute the tuning routine. The controller may include a digital system having primarily hardware devices such as an application specific integrated circuit (ASIC) or field-programmable gate array (FPGA), for example, or may include a combination of hardware and software, such as by a microprocessor system and a set of instructions to implement the controller's functionality. In other embodiments, the controller can be implemented as a combination of the two, with certain functions facilitated by hardware alone, and other functions facilitated by a combination of hardware and software. A variety of suitable microprocessor systems may be utilized including, without limitation, one or more microcontrollers, one or more digital signal processors, and the like, along with appropriate interfacing circuitry, data storage, power conditioning system, etc., as needed to implement the controller's functionality.

Figure 9A:
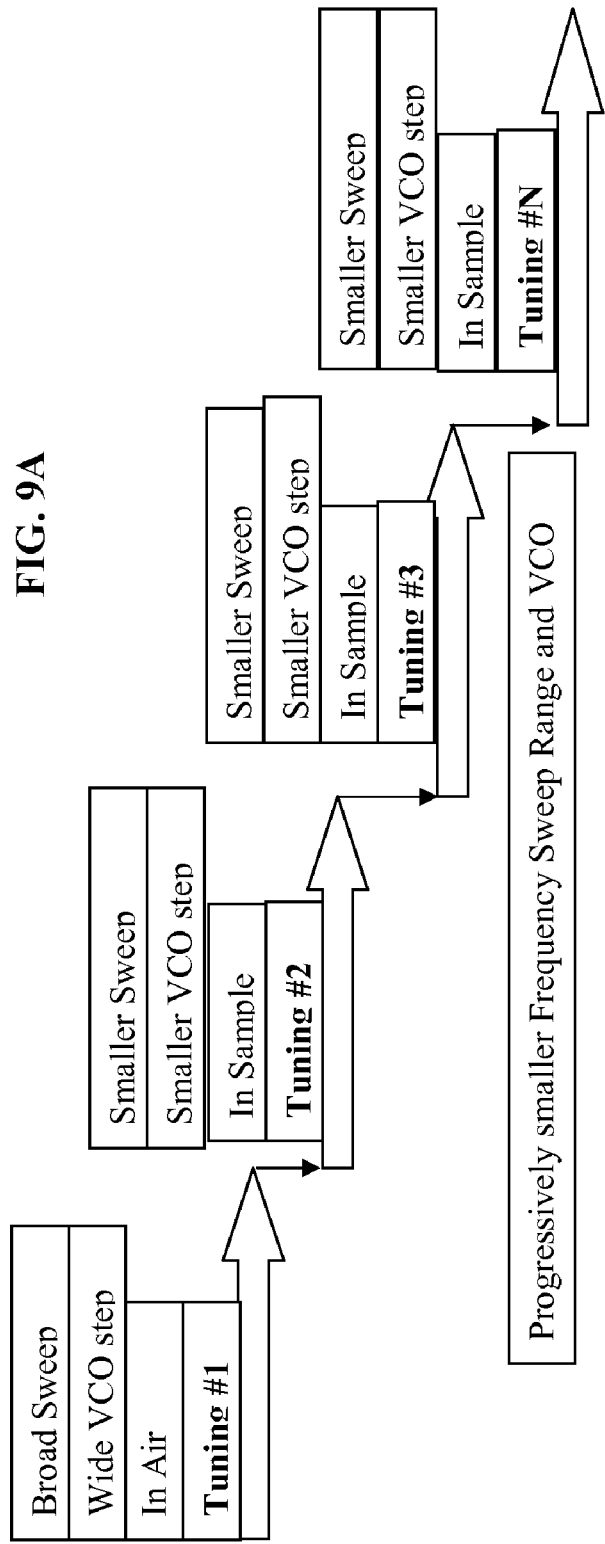
FIG. 9A is a diagram illustrating a multi-stage frequency sweep technique for in-situ tuning of a resonator according to one embodiment.
Figure 9B:
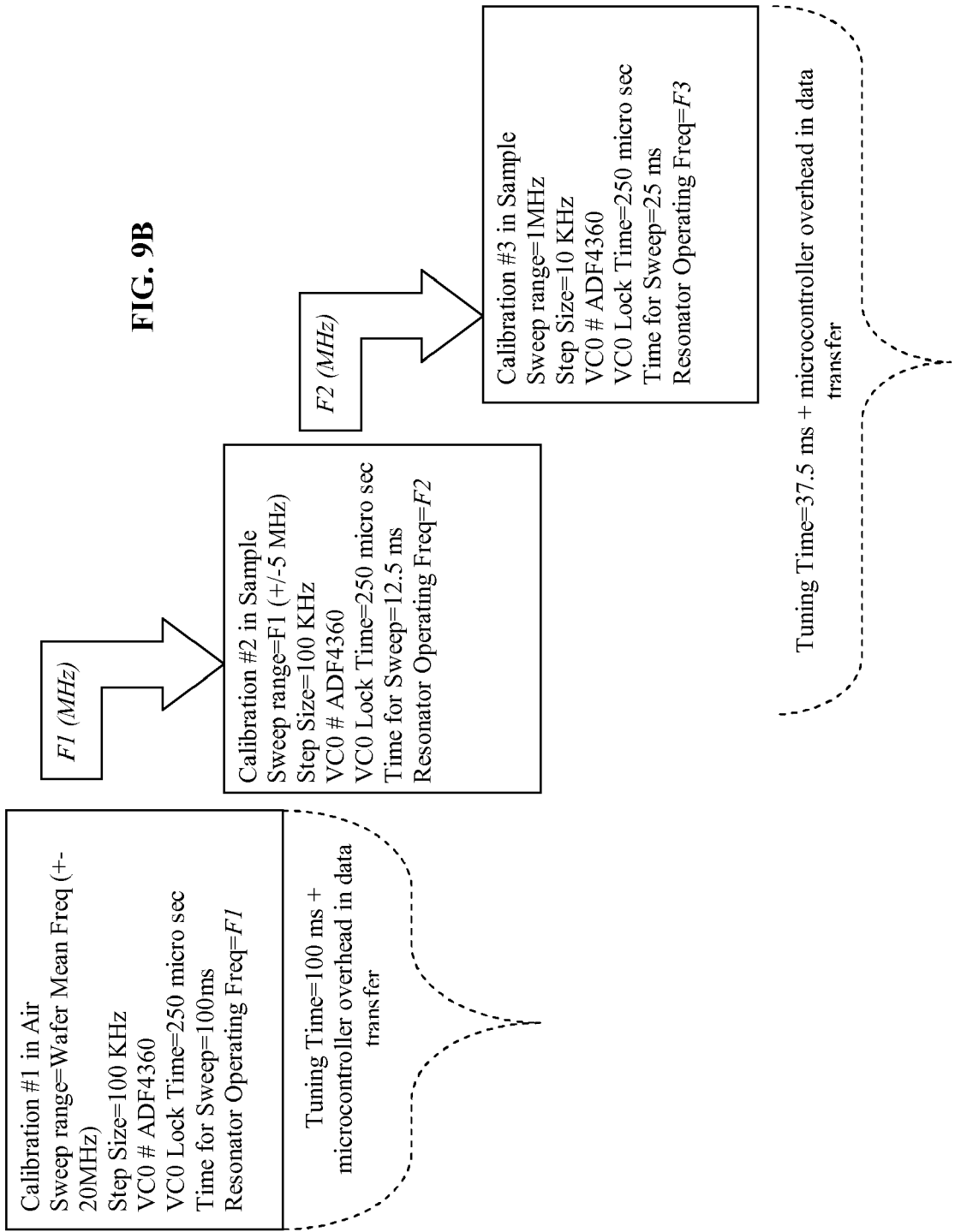
FIG. 9B is a diagram illustrating a practical implementation of the technique of FIG. 9A according to one embodiment.

Referring now to FIG. 9A, an efficient technique according to one embodiment for accomplishing a tuning sweep in a short time is illustrated. A first tuning step (performed while the resonator is in air—i.e., not yet placed in the sample) performs a relatively wide sweep range with a larger frequency step size setting for the VCO, or frequency generator. Successive fine-tuning (performed after the resonator is placed in the sample) progressively reduce the frequency sweep range with progressively smaller frequency step size. The number of steps that are employed is based on the assay characteristics and other variables such as microcontroller speed and bus communication performance. FIG. 9B is a diagram illustrating an example of such a scheme using an ADF4360 VCO as the frequency generator.

In a related embodiment, an even faster tuning is accomplished once the sensor is in a test sample with a modification of the second tuning step using a wider sampling interval that is intermediate between the intervals used in the first and second tuning steps in the example described above, to sweep through the +/−5 MHz window to identify, for example, a 1 MHz window within which a much finer sampling interval is used to achieve a more precise tuning Additional "nested" tuning steps may be used as needed and as hardware processing speeds allow to further improve precision and speed of tuning.

This more efficient method can be important in certain applications in which the test sample binds very quickly to the sensor. When a sensor comes into contact with a test sample the reaction of the capture ligand on the senor surface with the target in the sample begins immediately. It is therefore desirable for the optimum resonator operating frequencies to be determined in the shortest possible time following contact with test sample. Using the narrow bandwidth determined when tuned in air and then using the technique disclosed above addresses this need in a way not previously described by enabling tuning to be achieved within one second or less of sample contact. In one embodiment, tuning within 10 milliseconds is achieved. In a further embodiment, tuning within 5 milliseconds is achieved. In yet another embodiment, with sufficient processing capability, sensor tuning is achieved in less than one millisecond.

In one embodiment of the invention, the precise resonant frequency of each resonator is determined in air just prior to the introduction of the sensor into a test medium. By tuning the resonant frequency by sweeping through a range of approximately +/−3-5% of the resonator frequency prior to testing a first approximation of the resonant frequency of each resonator can be achieved with the methods discussed above used to analyze the response to the frequency sweep.

Additionally, in some embodiments an additional tuning process is performed immediately after (and in response to) the introduction of the sample to the sensor according to the exemplary process discussed above. In one example embodiment of the invention, each resonator is tuned to be driven at its ideal resonant frequency well within the first second of being introduced into the test medium. By tuning the resonant frequency by sweeping through a narrow range, for example, +/−5 MHz of the first approximation resonant frequency, a more exact resonant frequency can be used for testing. Other ranges may be appropriate depending on the base frequency of the resonator.

This in situ tuning has the advantage of further refining the driving resonant frequency of each resonator to take into account the transition from air to the test medium, such as a liquid solution. In the case where the target substance was known to instantly bind to a coating on the sensing resonator it may not be possible to perform an in situ tuning, but presently known coatings and target substances do provide many examples where the binding reaction can take longer than the time needed to perform the in situ tuning.

Examples of the operation of phase-shift and frequency-shift detector embodiments of instrument 12 will now be described with reference to FIGS. 10A-11B

Figure 10A:
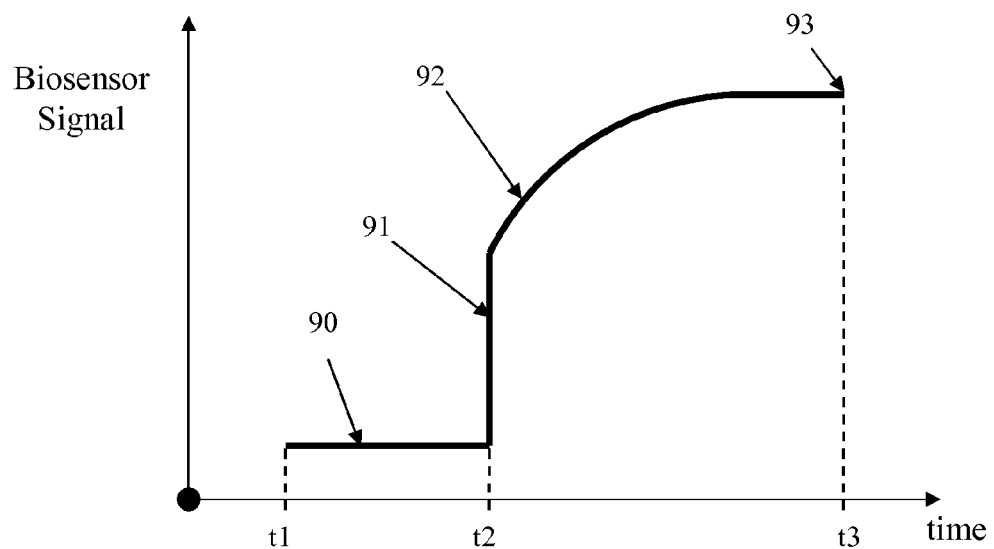
FIGS. 10A and 10B are graphs depicting evolution of biosensor signals over time during system operation for a frequency shift detection biosensor and a phase shift detection biosensor, respectively, according to embodiments of the invention.
Figure 10B:
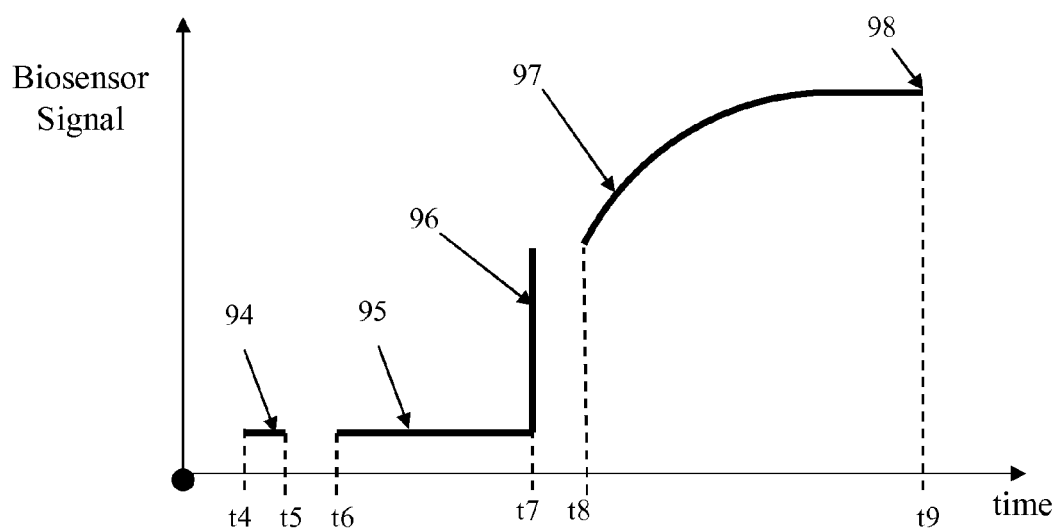

FIGS. 10A and 10B are graphs depicting evolution of biosensor signals over time during system operation for a frequency shift detection biosensor and a phase shift detection biosensor, respectively, according to embodiments of the invention. The biosensor signal may be phase, frequency, or some other metric indicative of the resonant behavior of the biosensor. The biosensor in these examples is intended for measurement of an analyte in liquid samples.

Referring first to FIG. 10A, initially, the biosensor is exposed to air (similarly, the biosensor may initially be exposed to another medium). At time t1 operation of the system is initiated either by application of power, automatic detection of biosensor connection, external activation by a user, or other such mechanism. After initiation at time t1 the biosensor output indicated at 90 is monitored by the electronics of the system while still in air or original medium (which is not the sample).

As detailed above, the monitoring apparatus according to various embodiments generally comprises a microcontroller-based system or the like that collects the biosensor signal at regular intervals. The monitoring apparatus may or may not record the collected biosensor signal. The monitoring apparatus continues to monitor the baseline biosensor output until an abrupt step change 91 is measured. The abrupt step change occurs due to introduction of a liquid sample into contact with the biosensor surface, causing the resonant properties of the biosensor to shift in response to the change in medium viscosity. For a given biosensor of a known construction, the approximate magnitude of the abrupt change will be known for a transition from air to liquid medium, thus providing a threshold, or target range of values, the achievement of which is deemed to be a sample introduction event. Using thresholding or a target range of values provides an advantage of ignoring small changes or noise in order to avoid false indications.

Thus, at time t2, liquid sample with unknown analyte concentration is placed in physical contact with the biosensor. In one embodiment, the abrupt biosensor signal step change 91 is used as a time reference representing the onset of liquid sample exposure on the biosensor surface. The abrupt signal change 91 will typically occur in less than 1 second, and often occurs in less than 0.1 seconds of sample introduction. Once the abrupt step change 91 is detected, the biosensor's output is monitored to measure the binding kinetics of analyte on the surface of the biosensor, as indicated at 92. In this embodiment tuning of the resonator is automatically handled by a control circuit. Therefore, measurement of the binding kinetics can begin as soon as the output is stabilized in response to introduction of the sample. This stabilization can occur in a matter of milliseconds, and in some embodiments in less than one millisecond.

The binding of analyte on the surface can be used to determine concentration of the analyte in the sample by any of a multitude of methods. One such method according to one embodiment involves measuring the rate of change of the biosensor output at stage 92. When measuring analyte concentration by rate of change, it is preferable according to one embodiment to measure the initial rate of change over a short time period very soon after the liquid sample is initially introduced to the biosensor surface. This early-stage measurement is commonly referred to as the initial on rate. As discussed above, especially for high concentrations of analyte and/or high association rates between analyte and capture ligand on the biosensor surface, an electronic time registration of initial liquid sample contact with biosensor surface (from abrupt biosensor output transient 91 at time t2) provides improved measurement accuracy and ability to measure faster binding rates.

The slope of biosensor output at 92 is proportional to the rate of analyte binding events on the biosensor surface. Over a range of analyte concentrations, the rate of analyte binding events on the biosensor surface is related to the concentration of analyte in the liquid sample. This relationship may be proportional or nonlinear, although proportionality may be preferred for the sake of accuracy and simplicity in practical embodiments. In this manner, the system uses accurate registration of time t2 to derive an accurate measure of analyte concentration in liquid sample that is accurate over a broad range of analyte concentrations.

A second method of determining analyte concentration according to a related embodiment is to measure the total amount of analyte bound over a fixed time interval t3–t2 by the total change of biosensor output (i.e., the level at time t3 minus the initial level at time t2). When measuring analyte concentration by total change over fixed time interval it is preferable to have an accurate measure of the initial start time for interaction between analyte and biosensor. As the fixed test time interval becomes smaller (for intentionally reduced test times such as in an emergency situations or for high analyte concentrations) accurate measurement of analyte and biosensor interaction time becomes increasingly important for making accurate analyte concentration measurements. Referencing the initial time of the time interval to the detected step change, the system of this embodiment uses accurate registration of time t2 to derive an accurate measure of analyte concentration in liquid sample that is accurate over a broad range of analyte concentrations.

FIG. 10B is a graph depicting similar operation using a phase detection arrangement such as the embodiments described above with reference to FIG. 3 and FIG. 4. At time t4, operation of the system is initiated (e.g., by application of power, automatic detection of biosensor connection, external activation by a user, or other means). After initiation at time t4 the system begins performing a tuning of the biosensor. This can be done for purposes of verifying proper function or optimizing operation at a preferred condition such as determining a resonant frequency. The tuning begins at time t5 and completes at time t6. The biosensor output at 94 can be logged as part of the test record, and may be useful in ascertaining the condition of the resonator or instrument. In a related embodiment, the interval between t4 and t5 may be eliminated with initial activation comprising the tuning operation.

Based on tuning of the biosensor, the desired operating condition is set for optimal operation at time t6 and the biosensor output at 95 is monitored by the electronics of the system while still in the original medium (e.g., air). The monitoring apparatus continues to monitor the biosensor output until an abrupt step change 96 is measured. At time t7, a liquid sample with unknown analyte concentration is placed in physical contact with the biosensor. Once the abrupt transient 96 is detected, the system performs a re-tuning for operation in the liquid sample. The re-tuning is performed between times t7 and t8. At time t8 the operating condition is set for optimal operation (e.g., at the point of resonance) and the biosensor output at 97 is monitored to measure the binding kinetics of analyte on the surface of the biosensor.

Particularly for high concentrations of analyte and/or high association rates between analyte and capture ligand on biosensor surface (i.e., avidity), an electronic time registration of initial liquid sample contact with biosensor surface (from abrupt biosensor output transient 96 at time t7) provides improved measurement accuracy and ability to measure faster binding rates. Furthermore, it is preferable for the re-tuning to be performed in a short period of time such that initial on rate is not missed during the process of re-tuning. In one embodiment, the re-tuning is performed in less than 1 second, and more preferably, the re-tuning is performed in less than 0.1 second. In general, the slope of biosensor output 97 is proportional to the rate of analyte binding events on the biosensor surface. Over a range of analyte concentrations, the rate of analyte binding events on the biosensor surface is related to the concentration of analyte in the liquid sample (preferably, in proportion). In this manner, the system uses accurate registration of time t7 and rapid re-tuning to derive an accurate measure of analyte concentration in liquid sample that is accurate over a broad range of analyte concentrations.

The second method of determining analyte concentration by measuring the total amount of analyte bound over a fixed time interval t9-t8 is also available in the phase change detection instrument. When measuring analyte concentration by total change over the fixed time interval, it is preferable to have an accurate measure of the initial start time for interaction between analyte and biosensor. It is further preferable to have minimal analyte-biosensor exposure time consumed by the re-tuning. As the fixed test time interval becomes smaller (for intentionally reduced test times such as in an emergency situation or for high analyte concentrations) accurate measurement of analyte and biosensor interaction time becomes increasingly important for making accurate analyte concentration measurements. In this manner, the system according to this embodiment uses accurate registration of time t8 and rapid re-tuning to derive an accurate measure of analyte concentration in liquid sample that is accurate over a broad range of analyte concentrations.

Figure 11A:
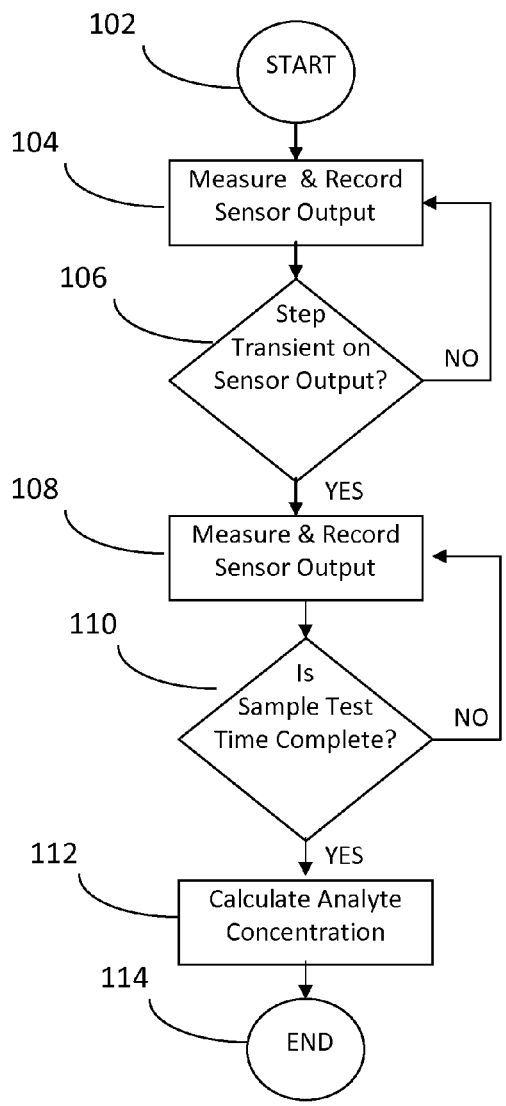
FIGS. 11A and 11B are a flow diagrams illustrating an exemplary operation, respectively, of systems that control and monitor the frequency shift detection biosensor, and the phase shift detection biosensor, the outputs of which are represented in FIGS. 10A and 10B above according to embodiments of the invention.
Figure 11B:
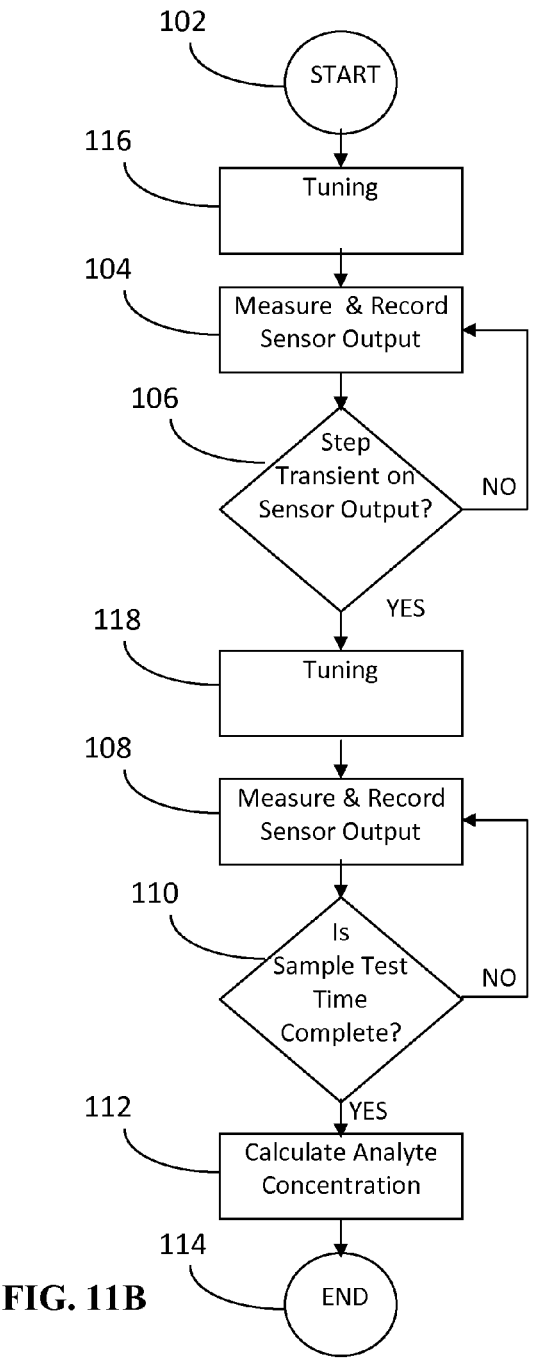

FIGS. 11A and 11B are a flow diagrams illustrating an exemplary operation, respectively, of systems that control and monitor the frequency shift detection biosensor, and the phase shift detection biosensor, the outputs of which are represented in FIGS. 10A and 10B above according to embodiments of the invention. In various embodiments, the block functions in FIGS. 11A and 11B are carried out under program control, e.g., as microcontroller firmware executed on a microcontroller or digital signal processor, with characteristic execution speed related to the circuit's architecture and clock frequency. Data acquisition operations such as block 104 that measures and records biosensor output may also involve analog-to-digital conversions (ADC) requiring multiple clock cycles or delays. In general, it is contemplated that each of the blocks can be executed in much less than 1 second, and preferably less than 1 millisecond. Fast electronic operation through each functional block provides for high accuracy measurements of analyte concentration in liquid samples.

Referring to FIG. 11A, operation of the system is initiated at 102, either by application of power, automatic detection of biosensor connection, external activation by a user, or other such mechanism. At 104, the system monitors and records output from the biosensor, typically measuring resonant frequency or phase angle offset relative to the driving signal. After each measurement, the system compares the most recent measurement to a previous measurement to determine if an abrupt biosensor signal change has occurred at decision 106. A choice function (typically including the difference between current and a previous measurement compared against a threshold or target range of minimum and maximum values corresponding to the anticipated step change range of values) is executed to decide if liquid sample has come into contact with the biosensor surface.

If an abrupt biosensor signal change has not occurred, execution loops back to monitoring and recording of additional biosensor output values at block 104. The 106-104 loop performs a "wait" operation in which the system monitors the biosensors output signal and waits for an abrupt change in the biosensor signal indicative of transition from air to liquid medium at the biosensor interface. The loop time constant, or repetition rate, is generally less than 1 second, and preferably less than 1 millisecond. Smaller loop time constants provide for more accurate measurement of the initial time of liquid introduction on biosensor surface.

If an abrupt biosensor signal change meeting the threshold or other criteria has occurred, execution control proceeds to 108 to monitor the binding of analyte on the biosensor surface. Here, the system executes continuous monitoring of the biosensor signal output in the loop 110-108. After each measurement in block 108, the total time of liquid exposure is evaluated in decision 110 to determine if the test is complete. For example, in the operation depicted in FIG. 10A, the test is completed at time t3. This 110-108 loop has a characteristic periodicity in time, or repetition rate that is typically less than 1 second, and preferably less than 1 millisecond. Once the desired test time is complete, the process continues to block 112, where analyte concentration is calculated based on the recorded data, either from initial rate of change or as final endpoint value (i.e., 93 in FIG. 10A). Calculation of analyte concentration may include recording or transmission of data, followed by transfer to execution control to termination or completion of the program at 114.

Referring now to FIG. 11B, a similar process is depicted for a phase shift detection biosensor. The numbered blocks 102-114 represent the correspondingly numbered blocks described above with reference to FIG. 11A. In this process, however, the additional sub-processes of tuning are performed at 116 and 118. Tuning is performed in air at 116 prior to initiating the measure and record operation at 104. The placement of this first tuning operation at this stage can maximize the sensor's sensitivity so that comparisons against the threshold at 106 in the determination of the step change are trustworthy. In one embodiment, the first tuning operation is performed immediately in response to initiation of operation.

The second tuning operation takes place in response to the detection of exposure of the resonator to the liquid sample at 106. In a preferred embodiment, this second tuning operation at 118 is performed as soon as possible upon the detection of the step change. The second tuning operation can be performed in well under one second, and preferably within a millisecond of the detection of the step change. The duration of the tuning procedure itself should also be performed in as short a time as practicable according to one embodiment. Thus, for instance, the tuning at 118 is performed within one second and, preferably within 0.1 second. Even more preferably, the tuning at 118 is accomplished within 50 milliseconds. For instance, in the embodiment described above with reference to FIG. 9B, tuning is accomplished in 37.5 milliseconds. It is contemplated that advances in processing capacity and in analog microelectronics will permit faster performance of the tuning operations.

In a related embodiment, the measure and record sensor output operation at 108 is initiated immediately, i.e., as fast as possible, in response to completion of the tuning operation at 118. In a practical embodiment this should be done within one second, and preferably within one millisecond. The first and the second tuning operations 116 and 118, in various embodiments, can be performed as detailed above with reference to FIGS. 9A and 9B.

In a related embodiment, where a sensing and reference resonator are utilized, the tuning operations 116 and 118 are performed on each of the resonators. In one such system, the resonators are tuned at about the same time, rather than sequentially one after the other.

In another sensing-and-reference resonator embodiment, the individual resonator output of either the sensing resonator alone, the reference resonator alone, or of both resonators in common mode (i.e., not differential mode), is monitored to detect the introduction of the sample. Measurement of binding kinetics, on the other hand, is based on the differential mode between the sensor and reference devices, as discussed above.

More generally, the step change detected at 106 more generally represents a change from one fluid viscosity characteristic to another. For instance the change can be from liquid to a gas, or from a liquid of a first density to a liquid of a second, different, density. In a related embodiment, the instrument is configured with an appropriate threshold or step change value target range corresponding to the expected change in viscosity from initiation of operation at 104 and introduction of the sample. This information can be stored, for instance, along with the calibration constants or other parameters specific to the biosensor assembly or test protocol in a data storage device such as the one described above, or in a remote but accessible location such as a personal computer workstation or server.

The embodiments above are intended to be illustrative and not limiting. Additional embodiments are within the claims. In addition, although aspects of the present invention have been described with reference to particular embodiments, those skilled in the art will recognize that changes can be made in form and detail without departing from the scope of the invention, as defined by the claims.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention may comprise a combination of different individual features selected from different individual embodiments, as will be understood by persons of ordinary skill in the art.

Any incorporation by reference of documents above is limited such that no subject matter is incorporated that is contrary to the explicit disclosure herein. Any incorporation by reference of documents above is further limited such that no claims that are included in the documents are incorporated by reference into the claims of the present Application. The claims of any of the documents are, however, incorporated as part of the disclosure herein, unless specifically excluded. Any incorporation by reference of documents above is yet further limited such that any definitions provided in the documents are not incorporated by reference herein unless expressly included herein.

For purposes of interpreting the claims for the present invention, it is expressly intended that the provisions of Section 112, sixth paragraph of 35 U.S.C. are not to be invoked unless the specific terms "means for" or "step for" are recited in a claim.

The invention claimed is:

1. Apparatus for measuring binding kinetics of an interaction of an analyte material present in a fluid sample comprising:
  a resonator interface adapted to be operatively coupled with one or more resonating devices, at least one of which is a sensing resonator having binding sites for the analyte material, wherein the one or more resonating devices are adapted to be driven into an oscillating motion by actuation circuitry;
  measurement circuitry arranged to be coupled to the one or more resonating devices via the resonator interface, and wherein the measurement circuitry is configured to measure one or more resonator output signals representing a resonance characteristic of the oscillating motion of the one or more resonating devices; and
  a controller operatively coupled with the actuation and measurement circuitry, the controller being interfaced with data storage containing instructions executable by the controller that, when executed, cause the controller to:
    detect introduction of the fluid sample into contact with the one or more resonating devices based on detection, via the measurement circuitry, of a characteristic change in the one or more resonator output signals caused by the introduction of the fluid sample; and
    in response to the detection of the introduction of the fluid sample, initiate measurement, via the measurement circuitry, of the binding kinetics of the analyte material to the at least one sensing resonator;
  wherein the characteristic change in the one or more resonator output signals caused by the introduction of the fluid sample causes a change to a new resonance point in the oscillating motion of the one or more resonating devices, and wherein the one or more resonating devices are driven at the new resonance point in response to the characteristic change in the one or more resonator output signals.

2. The apparatus of claim 1, wherein each of the one or more resonating devices is a bulk acoustic wave device having a resonant frequency in the range of several hundred megahertz to several gigahertz.

3. The apparatus of claim 1, wherein the resonator interface is further adapted to be operatively coupled with a reference resonator that lacks any binding sites for the analyte material, and wherein the reference resonator is adapted to be driven by the actuation circuitry having provisions for driving the at least one sensing resonator and the at least one reference resonator at different resonant frequencies.

4. The apparatus of claim 1, wherein the controller is further configured to monitor the one or more resonator output signals from a time reference based on the time of occurrence of the characteristic change in the one or more resonator output signals.

5. The apparatus of claim 1, wherein the controller is further configured to detect a step change in a resonant characteristic of the one or more resonating devices selected from the group consisting of: a frequency, a phase angle, or any combination thereof.

6. The apparatus of claim 1, wherein the controller is further configured to initiate measurement of the binding kinetics of the analyte material by initiating measurement of a rate of change of the one or more resonator output signals within one second of the detecting of the introduction of the fluid sample.

7. The apparatus of claim 1, wherein the controller is further configured to initiate measurement of the binding kinetics of the analyte material by initiating measurement of a rate of change of the one or more resonator output signals within 0.1 second of the detecting of the introduction of the fluid sample.

8. The apparatus of claim 1, wherein the controller is further configured to initiate measurement of the binding kinetics of the analyte material by initiating measurement of a total amount of change of the one or more resonator output signals time-referenced from the detection of the characteristic change in the one or more resonator output signals.

9. The apparatus of claim 1, wherein the controller is further configured to determine a measure of concentration of the analyte in the fluid sample based on the binding kinetics.

10. The apparatus of claim 1, wherein the controller is further configured to detect introduction of the fluid sample into contact with the one or more resonating devices by comparing a degree of the characteristic change in the one or more resonator output signals against a threshold value or target range of values such that false detections are suppressed.

11. A system for measuring binding kinetics of an interaction of an analyte material present in a fluid sample with one or more resonating devices, at least one of which is a sensing resonator having binding sites for the analyte material, the system comprising:
   means for initiating operation of the one or more resonating devices that produces one or more resonator output signals representing a resonance characteristic of each of the one or more of the resonating sensors;
   means for automatically detecting introduction of a fluid sample to the one or more resonating devices based on detection of a characteristic change in the one or more resonator output signals caused by the introduction of the fluid sample; and
   means for initiating automated measurement of the binding kinetics of the analyte material to the at least one resonating sensor having the binding sites in response to the detecting of the introduction of the fluid sample;
   wherein the characteristic change in the one or more resonator output signals caused by the introduction of the fluid sample causes a change to a new resonance point in the oscillating motion of the one or more resonating devices and wherein the one or more resonating devices are driven at the new resonance point in response to the characteristic change in the one or more resonator output signals.

12. The apparatus of claim 1, wherein the actuation circuitry is part of the resonator interface.

13. The apparatus of claim 1, wherein the actuation circuitry is configured to drive the one or more resonating devices at the new resonance point in response to the characteristic change in the one or more resonator output signals prior to the initiation of the measurement.

14. The apparatus of claim 1, wherein the instructions executable by the controller, when executed, further cause the controller to cause the actuation circuitry is to drive the one or more resonating devices at the new resonance point.

* * * * *